United States Patent
Lassen et al.

(10) Patent No.: US 6,790,611 B2
(45) Date of Patent: Sep. 14, 2004

(54) ASSAY FOR DIRECTLY DETECTING A RS VIRUS RELATED BIOLOGICAL CELL IN A BODY FLUID SAMPLE

(75) Inventors: Michael Rud Lassen, Rungsted Kyst. (DK); Morten Breindahl, Kg. Lyngby (DK)

(73) Assignee: Besst-Test APS, Rungsted Kyst (DK)

( * ) Notice: Subject to any disclaimer, the term of this patent is extended or adjusted under 35 U.S.C. 154(b) by 0 days.

(21) Appl. No.: 09/978,272

(22) Filed: Oct. 17, 2001

(65) Prior Publication Data

US 2002/0081573 A1 Jun. 27, 2002

Related U.S. Application Data

(60) Provisional application No. 60/242,132, filed on Oct. 23, 2000.

(30) Foreign Application Priority Data

Oct. 17, 2000 (DK) .......................................... 2000 01549

(51) Int. Cl.[7] ................................................. C12Q 1/70
(52) U.S. Cl. ........................... 435/5; 436/501; 436/518; 435/7.1
(58) Field of Search ............................ 435/5, 7.1, 7.92, 435/7.94, 975; 436/501, 518, 528, 529, 530

(56) References Cited

U.S. PATENT DOCUMENTS

| | | | | |
|---|---|---|---|---|
| 4,452,773 A | * | 6/1984 | Molday | ..................... 424/1.37 |
| 5,075,078 A | * | 12/1991 | Osikowicz et al. | ........... 422/86 |
| 5,543,332 A | * | 8/1996 | Lihme et al. | ................ 436/528 |
| 5,762,905 A | * | 6/1998 | Burton et al. | ............... 424/1.49 |
| 6,077,511 A | * | 6/2000 | Langedijk | ................. 424/186.1 |
| 6,083,708 A | * | 7/2000 | Singh et al. | ................ 435/7.92 |

FOREIGN PATENT DOCUMENTS

| | | | |
|---|---|---|---|
| EP | 0267317 | 5/1988 | |
| EP | 0420170 | 4/1991 | |
| EP | 0577092 | 1/1994 | |
| EP | 0957364 | * 11/1999 | ......... G01N/33/532 |
| EP | 0967484 | 12/1999 | |
| WO | 9015327 | 12/1990 | |
| WO | 9713150 | 4/1997 | |
| WO | 98/38513 | * 9/1998 | ......... G01N/33/541 |

OTHER PUBLICATIONS

Sheeran et al. Pediatric infectious disease journal 18(2):115–22, abstract only cited.*
Swiekosz et al (Journal of Clinical Microbiology 27:1151–1154, 1989).*
Tsutsumi et al (Journal of Clinical Microbiology 37:2007–2009, 1999).*
Ouchi et al (J. Infect. Chemother. 5:220–222, 1999).*

* cited by examiner

*Primary Examiner*—Mary E. Mosher
(74) *Attorney, Agent, or Firm*—Iver P. Cooper

(57) ABSTRACT

The present invention relates to a kit and an assay method for rapidly and directly detecting a predetermined respiratory syncytial virus-related biological cell in a sample, even when present in an amount of less than about 2000 cells per microliter. In a preferred embodiment, a labeled antibody targets a nucleoprotein or a glycoprotein of RS virus. One may further detect an inflammatory indicator in the sample.

70 Claims, 2 Drawing Sheets

ASSAY FOR DIRECTLY DETECTING A RS VIRUS RELATED BIOLOGICAL CELL IN A BODY FLUID SAMPLE

The present application claims the benefit of U.S. Provisional Appln. No. 60/242,132, filed Oct. 23, 2000.

TECHNICAL FIELD

The present invention relates to a method for rapid detection of a Respiratory Syncytial virus (RS virus) related biological cell and/or biological particle contained in a body fluid sample. The method is used for rapidly diagnosing a condition in an individual resulting from an infection by a RS virus.

The method comprises the further steps of detecting a plurality of infection and/or inflammatory response agents, preferably cytokines, and performing a profile of such agents. The profile is a further indication of the condition being diagnosed. The method for detecting a plurality of infection response agents, preferably cytokines, includes the step of performing a profile of such agents.

The methods of the invention are performed by contacting i) a body fluid sample potentially comprising the infectious agent and/or an infection and/or inflammatory response agent, including cytokines, with ii) a targeting species that is preferably quantifiably detectable and capable of specifically recognising a predetermined infectious agent and/or a predetermined infection response agent. It is preferred that the contacting takes place essentially without pretreatment of the body fluid sample.

The targeting species preferably comprises an antibody capable of contacting one or both of an infectious agent and an infection response agent. The targeting species may also comprise a visible label capable of being detected when the complex of the targeting species with either one or both of an infectious agent and an infection response agents is in contact with a solid test area on e.g. a lateral flow device.

BACKGROUND OF THE INVENTION

Antigens from microbial cells have been detected in the prior art. U.S. Pat. No. 4,663,277 relates to a method for detecting a virus by means of an immunoassay in which an extended solid phase coated with antiviral antibody is employed to bind and remove virions from a specimen by forming an immuno-complex with antigens of said virions, a mobile solid phase comprising a dispersion of microspheres coated with the antiviral antibody is used to bind said microspheres to antigens associated with said Immuno-complex, and the presence of bound microspheres is detected. The detection sensitivity is amplified by using microspheres comprising a dye or a label. The extended solid phase may be in the form of a dipstick, syringe, tube or container that can be easily contacted with the specimen. A virus detection kit provides the extended solid phase and mobile solid phases, each coated with antiviral antibodies.

In one embodiment the invention disclosed in U.S. Pat. No. 4,663,277 pertains to a method for detection of viruses in a specimen and comprises the steps of i) treating the specimen to remove undesired components ii) contacting the specimen with a solid phase support having conjugated thereto antiviral antibody capable of forming immuno-complexes with antigens characteristic of the viruses to be detected, iii) separating the solid phase support from the specimen, iv) contacting the separated solid phase support with a mobile solid phase consisting of dispersed microspheres smaller than 0.1 $\mu$m and labelled with metal elements and having conjugated thereto the antiviral antibody that enables the binding of said microspheres to said immuno-complexes, v) separating the unbound mobile solid phase from the solid phase support, and vi) measuring the presence of microspheres bound to said solid phase support by X-ray fluorescence, thereby detecting or determining the presence of viruses in said specimen.

An antispecies antibody is covalently bound to the solid phase support as well as to the mobile solid phase, and an antiviral antibody that forms an immuno-complex with the antispecies antibody is coupled therewith, whereby an antiviral antibody capable of forming immuno-complexes with antigens of viruses to be detected is conjugated to said solid phase support and to said mobile solid phase.

In one embodiment of the invention a plurality of different antiviral antibodies capable of forming complexes with corresponding antigens of different types of viruses are conjugated to the solid phase support as well as to the mobile solid phase, whereby the presence of one or more of a plurality of different types of viruses in the specimen can be detected at the same time.

U.S. Pat. No. 4,740,467 discloses a method for diagnosing syphilis and other treponematoses infections such as yaws and pinta. The method involves admixing i) a biological sample, such as lesion exudate, cerebrospinal fluid, serum, urine, amniofic fluid, synovial fluid or tissue homogenate from a person suspected of having syphilis, yaws or pinta together with ii) a reagent of monoclonal antibodies which are specific for antigens of virulent subspecies of *Treponema pallidum*, including *pertenue, endemicum, carateum* and *pallidum*. If *Treponema pallidum*, the causative organism of syphilis, is present, an immunological specific binding reaction will occur between the monoclonal antibodies and antigenic sites on *T. pallidum* cells. A positive immunoreaction is detected directly by a variety of techniques including radioimmunoassay, fluorescent immunoassay, enzyme linked immunosorbent assay, agglutination reactions, and complement consumption tests.

U.S. Pat. No. 5,290,677 discloses a method for detecting hepatitis A virus by capturing whole virus particles with antibodies specific to hepatitis A virus. In subsequent steps the method comprises generating a cDNA copy of the RNA by reverse transcription in the presence of a primer having a predetermined sequence, amplifying the cDNA by a polymerase chain reaction, and detecting the amplified cDNA by hybridization with probes of a predetermined sequence, or by detection of label bound to the primer, wherein the presence of detectable hybridization or amplification indicates the presence of hepatitis A virus. It is disclosed that samples which contain free virus (for example, stool, environmental samples, or other fomite associated material) may be selectively removed from adventitious material by immunoselection of whole virus using a high titer anti-HAV antibody coated onto a solid phase. The viral RNA is then denatured in the presence of a specific primers, and the viral RNA is reverse transcribed to cDNA using standard methodology.

Further examples of diagnostic methods pertaining to the detection of microbial cells are disclosed e.g. in U.S. Pat. No. 6,077,665 relating to a rapid assay for infection in immunodeficient patients such as neonates or immunocompromised patients (e.g. HIV or transplant patients). The method allows diagnosis at initial evaluation, such that antibiotic treatment and confinement to an intensive care unit can be avoided for uninfected patients. The assay can be used for sepsis diagnosis including the detection of bacterial, viral, or fungal colonization of the blood stream, cerebrospinal fluid (CSF), or urinary tract. The method is based on the measurement of polymorphonuclear leukocyte (PMN, neutrophil) CD11b (Mac-1, CR3) levels by flow cytometry or laser scanning microscopy in whole blood samples.

U.S. Pat. No. 5,965,354 relates to a method and immunodiagnostic test kits for diagnosing herpes simplex virus infection. The methods and kits employ type-specific or type-common antigens in a single-step assay format. In one embodiment the method of the invention comprises the steps of i) contacting a biological sample from a human suspected of containing antibodies to herpes simplex virus with one or more purified herpes simplex virus polypeptides bound to a solid support, under conditions that allow herpes simplex virus antibodies, when present in the biological sample, to bind to said herpes simplex virus polypeptides, and ii) detecting the presence or absence of bound antibodies as an indication of the presence or absence of herpes simplex virus, wherein said detecting is done by using at least one detectably labeled anti-human immunoglobulin antibody.

U.S. Pat. No. 5,939,254 discloses specific primers that amplify a portion of the 3'-noncoding regions of a dengue virus, and a method of using these primers in a rapid reverse transcriptase-polymerase chain reaction (RT-PCR) for specific detection of dengue viruses.

U.S. Pat. No. 5,919,616 relates to serological detection of a herpes simplex virus infection by means of reaction of a patient serum sample potentially containing virus antibody with a virus specific peptide that may be used in an assay including an enzyme linked immunosorbent assay (ELISA).

U.S. Pat. No. 5,744,299 is concerned with a method for evaluating a biological sample for the presence or absence of human parainfluenza virus and for the quantitation of the virus The method comprises the steps of isolating RNA from the biological sample, generating cDNA from the isolated RNA, amplifying the generated cDNA, and determining virus infection by detecting the amplified sequence.

U.S. Pat. No. 5,695,930 relates to a method for detecting antibodies to a human immunodeficiency virus and comprises the steps of i) contacting saliva from a human with p17 protein from human immunodeficiency virus bound to a nitrocellulose-containing solid support for a time and under conditions sufficient for an antibody in the saliva to said antigen to form a complex therewith, and ii) subjecting the complex to detecting means in order to detect the complex.

U.S. Pat. No. 5,660,979 discloses a method for determining virus replication in human cells by human retrovirus using RNA amplification and comprises the step of detecting the hybridization of an RNA probe which specifically hybridizes with spliced RNA and not with genomic RNA. The method permits early detection of RNA replication resulting from primary infection without detecting non-replicating virus.

U.S. Pat. No. 5,643,714 relates to HTLV gp21 envelope protein specific peptides for use in diagnostic assays for detecting and confirming HTLV infection in human sera. The invention also pertains to a kit for detecting the presence of HTLV infection in a human serum sample. The kit comprises i) a solid support and, ii) a peptide antigen attached to the solid support in a reaction zone, and iii) reporter means for detecting the presence of human antibodies bound to the support.

U.S. Pat. No. 5,593,849 discloses an immunochemical assay that uses enzyme-linked immunosorbence to detect the presence of antibodies against environmental protein sequences that mimic the human opioid peptide dynorphin in a human body fluid sample. The assay makes it possible to correlate and diagnose psychobiological or medical disorders related to alterations In the normal levels of dynorphin peptides or their receptors.

U.S. Pat. No. 5,587,285 describes a highly sensitive anti-HIV antibody detection assay. The assay detects the presence of anti-HIV antibodies through the use of a non-denatured HIV antigenic determinant which immunoreactivity binds anti-HIV antibodies in a biological sample. The non-denatured HIV antigenic determinant has provided a means for detecting anti-HIV antibodies in serum samples testing seronegative for the presence of HIV antibodies directed against denatured HIV antigens.

U.S. Pat. No. 5,565,319 relates to compositions derived from a viral isolate of feline T-tymphotropic lentivirus (FTLV) and antibodies to antigenic sites on the virus. The compositions are useful in a variety of techniques for the detection of and vaccination against FTLV. Detection methods disclosed include immunoassays. In one embodiment there is provided an enzyme-linked immunosorbent assay (ELISA) for detecting Feline Immunodeficiency Virus (FIV) antibodies. The assay comprises a solid phase coated with FIV antigen, wherein FIV antibodies in a sample exposed to the solid phase will bind to the antigen; and a detectable label conjugate which will bind to FIV antibodies bound to the solid phase.

U.S. Pat. No. 5,487,969 pertains to a method for detecting the presence of herpes B virus in an individual and comprises the steps of i) obtaining a sample from an individual suspected of being infected with herpes B virus, ii) extracting DNA from any herpes B virus, iii) amplifying segments of the extracted DNA by using predetermined primer sequences, iv) analyzing the amplified DNA segments by means of e.g. digesting the amplified DNA segments with a restriction enzyme, or by hybridizing the amplified DNA segments with a labeled oligonucleotide probe.

U.S. Pat. No. 5,225,322 relates to a method for detecting an antigen in a test sample suspected of containing said antigen, and simultaneously determining a fingerprint of antibodies specific for said antigen. The method comprises the steps of i) providing polyclonal antibodies specific for the antigen in question, ii) separating the polyclonal antibodies from each other according to the electrical charge of individual antibodies, iii) binding the separated antibodies to a solid support so that the antibodies separated in step ii) maintain the same relative position with respect to each other on the solid support, the relative position of the antibodies forming a fingerprint of antibodies specific for said antigen, iv) contacting the antibodies bound in step iii) with a test sample suspected of containing the antigen under conditions selected to allow binding of the antigen to the antibodies bound in step iii), v) contacting antigen bound in step iv) with detectably labeled antibodies specific for the antigen, under conditions selected to allow binding of said detectably labeled antibodies to said antigen, and vi) detecting the detectably labeled antibody as an indication of the presence of said antigen in the test sample, and revealing the fingerprint of antibodies that are specific for the antigen when the antigen is present in the test sample.

U.S. Pat. No. 5,212,062 is related to a method for detecting antigens from *Chlamydia psittaci* or *Chiamydia trachomatis* in a sample. The method comprises the steps of i) contacting a sample with a predetermined monoclonal antibody affixed to a solid support for a time and under conditions sufficient to form an immune complex on said support, ii) contacting the support with an antibody which binds to said antigen in said immune complex for a time and under conditions sufficient for binding to occur, and iii) detecting the presence of said immune complex as an indication of the presence of *Chlamydia psittaci* or *Chiamydia trachomatis* antigen in said sample.

U.S. Pat. No. 5,155,021 is directed to a method for the determination of a herpes simplex virus and comprises a first step i) of contacting a specimen suspected of containing herpes simplex viral antigen with polymeric particles which have a surface area of from about 0.1 to about 600 m$^2$/g of particles. Each particle is substantially free of any chemical or biological material and has an average diameter of from about 0.01 to about 10 µm. The particles are capable of directly binding herpes simplex viral antigen. Within about 10 minutes of contacting step i) A, herpes simplex viral antigen directly bound to the particles are contacted in a second step ii) with herpes simplex viral antibody so as to form an immunological complex on said particles. The bound complex is then separated from uncomplexed herpes simplex viral antibody by using a microporous membrane having an average pore size of from about 0.1 to about 20 µm. and the complex is determined as an indication of the presence of herpes simplex virus in said specimen. The method is carried out within about 30 minutes.

U.S. Pat. No. 5,093,230 relates to an assay method for detecting 1µM antibodies to a retrovirus selected from the group consisting of HIV-1, HIV-2, HTLV-I, and HTLV-II. The method is carried out within 70 minutes and comprises the steps of i) contacting nitrocellulose paper containing blotted, resolved retrovirus antigen protein obtained from gel electrophoroctically received viral lysate with a test sample, and incubating under predetermined conditions the nitrocellulose paper and test sample to permit binding of antibodies present in the sample to the protein on the nitrocellulose paper, iii) contacting the incubated nitrocellulose paper of step i) with an anti-IgM enzyme conjugated antiserum reactive with said antibodies, and incubating to permit binding of the antiserum to said antibodies, iii) contacting the incubated nitrocellulose paper of step ii) with an enzyme substrate specific for the enzyme of step ii), and incubating to produce a colour, iv) stopping the colour producing reaction of step iii); and v) evaluating the amount of colour produced as an indication of the presence of antibodies to the viral lysate.

A plurality of cytokines have been detected in the prior art. U.S. Pat. No. 5,587,294 relates to a method for measuring endogenous cytokines in blood. Cytokines are measured in the presence of substances that bind the cytokines and causes conventional methods to give inaccurate results. The invention also pertains to non-invasive measurement of cytokines in biological fluids such as saliva and nasal secretions. In one embodiment the invention relates to a method for monitoring cytokine therapy in a human, wherein the cytokine is able to bind a carrier molecule, with the proviso that the cytokine is not IL-1. The method comprises the steps of i) obtaining a human body fluid sample potentially comprising a cytokine, ii) forming an assay mixture by combining the sample from step i) with a) an antibody capable of binding specifically to substantially all of the cytokine, wherein the antibody is immobilized on a solid phase support, and b) a labeled binding epitope of the cytokine, wherein the labeled binding epitope competes with the cytokine for antibody binding, iii) incubating the assay mixture to allow the immobilized antibody to bind specifically to either the cytokine or the labeled binding epitope, iv) washing unbound, labeled binding epitope from the solid phase support, v) detecting bound label on the solid phase support, vi) determining the amount of the cytokine in the sample. In a further step the determination of the amount of cytokine is compared to the amount of the cytokine in the sample with a determination of the cytokine in a previous body fluid sample. Preferred cytokines are interleukin-2, interleukin-6, interferon-α, interferon-γ and tumor necrosis factor-α.

SUMMARY OF THE INVENTION

In a first aspect there is provided a kit for directly detecting a predetermined RS virus related biological cell present in a sample in an amount of less than about 2000 per microliter (10$^{-6}$ liter), said kit comprising i) a solid support and ii) a plurality of a first targeting species bound to the solid support, said targeting species being capable of directly detecting said predetermined RS virus related biological cell when it is present in a sample that is brought into contact with the solid support, and iii) a conjugate comprising a polymeric carrier molecule bound to at least
   a) one first and/or second targeting species being capable of directly detecting said predetermined RS virus related biological cell when it is present in a sample that is brought into contact with the solid support, and
   b) at least one labelling species.

In further aspects the invention relates to a method for detecting a RS virus related biological cell in a sample and a method for diagnosing and/or treating an infection in an individual.

The method of detecting a predetermined RS virus related biological cell present in a sample, preferably a body fluid sample, comprises the steps of
   i) contacting the sample with the kit according to the invention, and
   ii) detecting a targeting species capable of targeting the predetermined RS virus related biological cell,
wherein the detection of the targeting species is indicative of the presence of the RS virus related biological cell in the sample.

In another aspect there is provided a method for detecting at least one predetermined inflammatory indicator present in a sample in an amount of less than 100 nanograms (100× $10^{-9}$ grams) per milliliter ($10^{-3}$ liter). The method comprises the steps of
   i) contacting the sample with a kit comprising
      a) a solid support, and
      b) a plurality of a first targeting species bound to the solid support, said targeting species being capable of directly detecting said predetermined RS virus related biological cell when it is present in a sample that is brought into contact with the solid support, and
      c) a conjugate comprising a polymeric carrier molecule bound to i) at least one first and/or second targeting species capable of directly detecting said predetermined RS virus related biological cell when it is present in a sample that is brought into contact with the solid support, and ii) at least one labelling species, and
   ii) detecting a targeting species capable of targeting the predetermined inflammatory indicator,
wherein the detection of the targeting species is indicative of the presence of the predetermined inflammatory indicator in the sample.

By the term inflammatory indicator or agent is meant an indicator of inflammatory and/or immune system activity, such indicators for example being cytokines and autoantibodies.

In a further aspect there is provided a method for diagnosing a RS virus infectious condition in an individual, said method comprising the steps of
   i) detecting a predetermined RS virus related biological cell present in a body fluid sample according to the method of the invention, and
   ii) diagnosing said infectious condition.

In a still further aspect the invention pertains to a method for diagnosing a RS virus infectious condition in an individual, said method comprising the steps of
   i) detecting a predetermined RS virus related biological cell present in a body fluid sample according to a method of the invention,
   ii) detecting a predetermined inflammatory indicator present in a body fluid sample according to a method of the invention, and
   iii) diagnosing said infectious condition.

In yet another aspect there is provided a method for treating a RS virus infectious condition in an individual, said method comprising the steps of
   i) performing a diagnosis according to any of the methods of the invention, and
   ii) treating the RS virus infectious condition based on the diagnosis.

Still further aspects of the invention relates to a kit according to the invention for use in i) a method for detecting a predetermined RS virus related biological cell or a predetermined inflammatory indicator, ii) a method for diagnosing a RS virus infectious condition in an individual, and/or a method for treating a RS virus infectious condition in an individual.

DETAILED DESCRIPTION OF THE INVENTION

Figure 1:
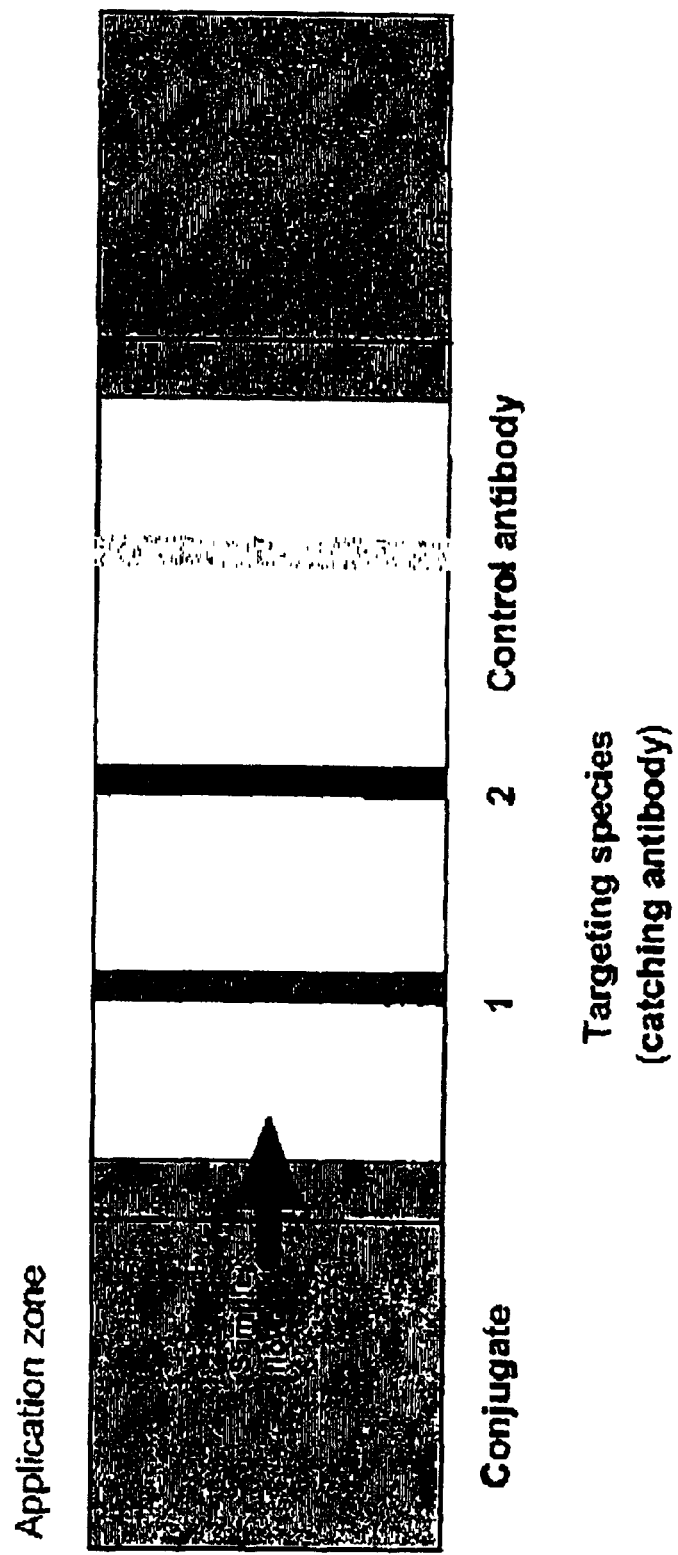
FIG. 1 illustrates a schematic dipstick, for use in an assay for testing detecting of RS related cell in a sample. The dipstick comprises an application zone for the sample comprising the reporter species. The term conjugate refers to reporter species.
Figure 2:
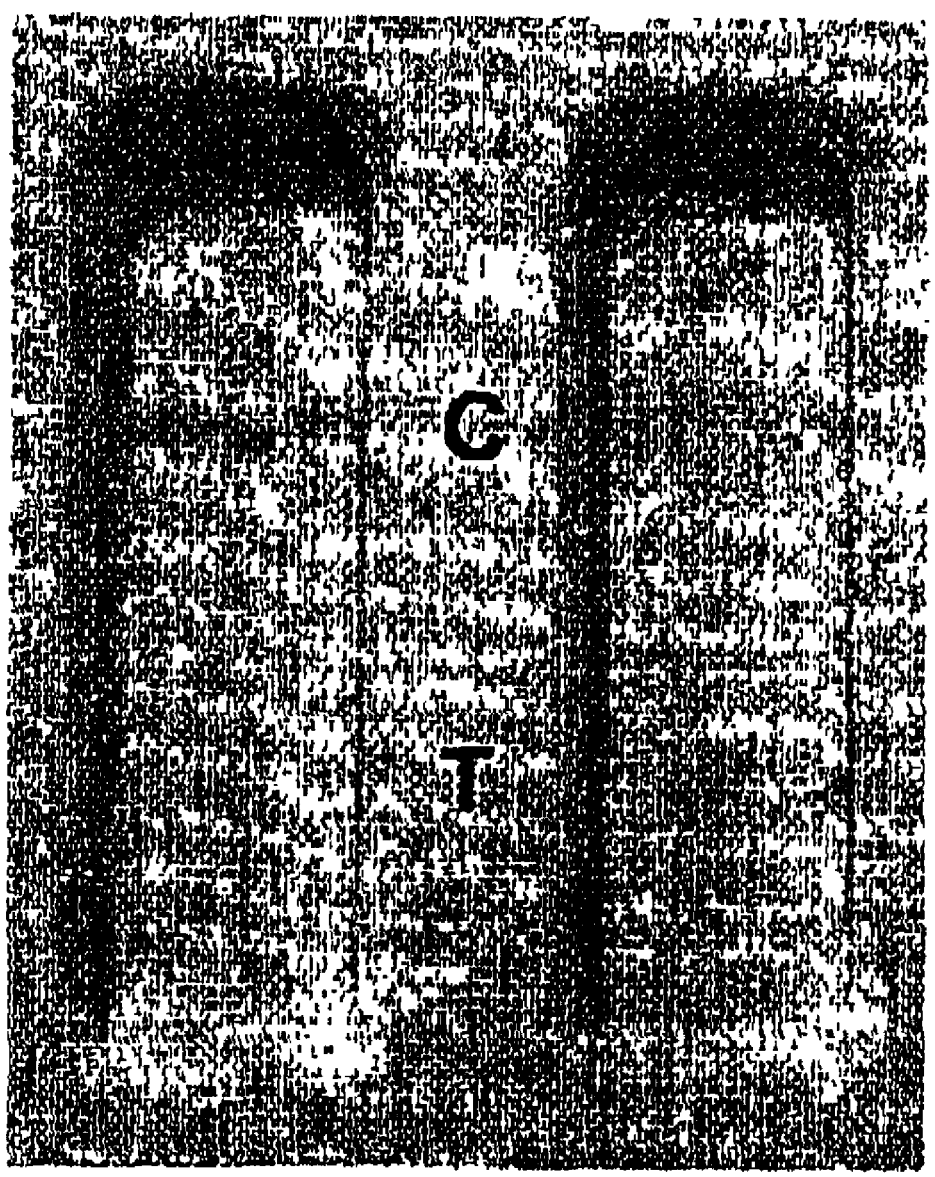
FIG. 2 illustrates a dipstick developed so that a red test line appears across the membrane instead of a red spot, both for observing the test result and the control.

In one preferred embodiment the present invention relates to a kit for directly detecting a predetermined RS virus related biological cell present in a sample in an amount of less than about 2000 per microliter ($10^{-6}$ liter), said kit comprising
   i) a solid support, and
   ii) a plurality of a first targeting species bound to the solid support, said targeting species being capable of directly detecting said predetermined RS virus related biological cell when it is present in a sample that is brought into contact with the solid support, and
   iii) a conjugate comprising a polymeric carrier molecule bound to at least
      a) one first and/or second targeting species being capable of directly detecting said predetermined RS virus related biological cell when it is present in a sample that is brought into contact with the solid support, and
      b) at least one labelling species,
wherein the polymeric carrier molecule comprises a plurality of at least one reactive, functional group, at least one connecting moiety attached to the at least one reactive, functional group, and at least one molecular species selected from the group of molecular species consisting of targeting species and labelling species.
wherein each of the molecular species comprises at least one functional group that is reactive with at least one connecting moiety attached to the reagent, and
wherein the conjugate comprises at least one molecular species covalently attached thereto via a connecting moiety.

The polymeric carrier molecule preferably comprises reactive, functional groups in an amount of from about 5 to about 5,000 μmoles per gram of polymeric carrier.

In another embodiment the polymeric carrier molecule comprising e.g. a dextran chain according to the invention comprises less than about 400 labelling species, preferably in the form of visibly detectable targeting species or fluorescently detectable labelling species, such as less than 380 labelling species, for example less than 360 labelling species, such as less than 340 labelling species, for example less than 320 labelling species, such as less than 300 labelling species, for example less than 280 labelling species, such as less than 260 labelling species, for example less than 240 labelling species, such as less than 220 labelling species, for example less than 200 labelling species, such as less than 180 labelling species, for example less than 120 labelling species, such as less than 140 labelling species, for example less than 120 labelling species, such as less than 100 labelling species, for example less than 80 labelling species, such as less than 70 labelling species, for example less than 60 labelling species, such as less than 50 labelling species, for example less than 40 labelling species, such as less than 30 labelling species, for example less than 25 labelling species, such as less than 20 labelling species, for example less than 15 labelling species, such as less than 12 labelling species, for example less than 10 labeling species, such as less than 8 labelling species, for example less than 4 labelling species, such as less than 3 labelling species, for example less than 2 labelling species.

The molecular weight of a polymeric dextran chain is preferably about 500,000 Da, but molecular weights from about 100,000 Da to about 900,000 Da can also be used.

Each dextran chain in one embodiment comprises approximately 2,700 glucose units of which 20–22% are activated, preferably with divinyl sulfon, although other connecting moieties can also be used as described herein below in detail.

In one embodiment about half of the about 600 connecting moieties, preferably, but not limited to, divinyl sulfon groups, per dextran chain react with targeting species and labelling species according to the invention, and this provides the figure of less than about 400 labelling species per dextran chain. However, it is clear that more than about half of the 600 connecting moieties may well react with a labelling species, and the number of labelling species may therefore be higher than about 400.

The number of labelling species and targeting species in a single polymeric carrier molecule according to the invention influences the minimum amount of biological cells including virus particles that can be detected according to the invention. In one embodiment the minimum amount of cells detectable is less than 2000 cells per microliter sample specimen, such as less than 1900 cells per microliter, for example less than 1800 cells per microliter, such as less than 1700 cells per microliter, for example less than 1600 cells per microliter, such as less than 1500 cells per microliter, for example less than 1400 cells per microliter, such as less than 1300 cells per microliter, for example less than 1200 cells per microliter, such as less than 1100 cells per microliter, for example less than 1000 cells per microliter, such as less than 900 cells per microliter, for example less than 800 cells per microliter, such as less than 700 cells per microliter, for example less than 600 cells per microliter, such as less than 500 cells per microliter, for example less than 450 cells per microliter, such as less than 400 cells per microliter, for example less than 350 cells per microliter, such as less than 300 cells per microliter, for example less than 280 cells per microliter such as less than 260 cells per microliter, for example less than 240 cells per microliter, such as less than 220 cells per microliter, for example less than 200 cells per microliter, such as less than 180 cells per microliter, for example less than 160 cells per microliter, such as less than 140 cells per microliter, for example less than 120 cells per microliter, such as less than 100 cells per microliter, for example less than 80 cells per microliter, such as less than 60 cells per microliter, for example less than 50 cells per microliter, such as less than 45 cells per microliter, for example less than 40 cells per microliter, such as less than 35 cells per microliter, for example less than 30 cells per microliter, such as less than 25 cells per microliter, for example less than 20 cells per microliter, such as less than 15 cells per microliter, for example less than 10 cells per microliter, such as less than 5 cells per microliter, for example less than 1 cell per microliter sample specimen.

In another embodiment of the invention the minimum amount of cells detectable is less than 1000 cells per milliliter, for example less than 900 cells per milliliter, such as less than 800 cells per milliliter, for example less than 700 cells per milliliter, such as less than 600 cells per milliliter, for example less than 500 cells per milliliter, such as less than 400 cells per milliliter, for example less than 300 cells per milliliter, such as less than 200 cells per milliliter, for example less than 150 cells per milliliter, such as less than 100 cells per milliliter, for example less than 90 cells per milliliter, such as less than 80 cells per milliliter, for example less than 70 cells per milliliter, such as less than 60 cells per milliliter, for example less than 50 cells per milliliter, such as less than 40 cells per milliliter, for example less than 30 cells per milliliter, such as less than 20 cells per milliliter, for example less than 10 cells per milliliter, such as less than 5 cells per milliliter, for example less than 3 cells per milliliter, such as less than 1 cell per milliliter sample specimen.

The RS virus related biological cell including a RS virus particle present in a sample specimen such as e.g. a body fluid sample is preferably detected and recorded as a positive diagnostic result according to one method of the invention in less than about 20 minutes, such as less than 15 minutes, for example less than 10 minutes, such as less than 8 minutes, for example less than 7 minutes, such as less than 6 minutes, for example less than 5 minutes, such as less than 4 minutes, for example less than 3 minutes, such as less than 2 minutes, for example less than 1 minute, such as less than 45 seconds, for example less than 30 seconds, such as less than 15 seconds.

The preferred statistical quality parameters for the present invention when the test is capable of detecting an amount of cells as specified above within a predetermined time period may be summarised as follows:

Sensitivity: at least 80% such as at least 85%, such as at least 90%.

Specificity; at least 80%, such as at least 85%, such as at least 90%.

Positive predictive value, at least 80%, such as at least 85%, such as at least 90%

Negative predictive value: at least 80%, such as at least 85%, such as at least 90%, more preferably at least 99.5%

The positive and the negative predictive value is closely related to the prevalence of the disease in the population to be tested. In the present context it is preferred that the statistical calculations are based on a type of population that are realistic for using the test. Thus, the statistical calculations are not based only on a population known to have acquired the disease, but also on individuals that might turn out as negatives for the disease. Due to the validity and sensitivity of the kit according to the present invention the kit is particular suitable for testing of populations having a prevalence of the condition being tested for less than 100%, such as less than 90%, such as less than 80%, more preferably less than 70%, even more preferred less than 60%, such as about 50%.

The present invention provides in another embodiment a method for detection of biological cells including viruses in a specimen, wherein said specimen, optionally treated to remove undesired components, is contacted with an extended solid phase having conjugated thereon a targeting species, preferably an antibody, directed against the RS virus related biological cell including a virus. The contacting results in the case of an antibody being used in the formation of immuno-complexes with antigens characteristic of the biological cells and viruses to be targeted.

The extended solid phase is separated from the specimen; said separated extended solid phase is contacted with a mobile solid phase comprising a polymeric carrier molecule according to the invention having conjugated thereto a predetermined targeting species such as an antibody. The antibody results in the binding of said polymeric carrier molecules according to the invention to said immuno-complexes; the extended solid phase is subsequently separated from said mobile solid phase, and the presence of polymeric carrier molecules according to the invention bound to said extended solid phase is detected, whereby the presence of biological cells including viruses in said specimen is detected or determined.

Also, the invention provides a RS virus related biological cell detection kit and virus detection kit which comprises as individual components: (a) an extended solid phase having conjugated thereon a targeting species, preferably an antibody capable of forming immuno-complexes with antigens characteristic of the biological cells and viruses to be detected; and (b) a mobile solid phase consisting of dispersed polymeric carrier molecules according to the invention having conjugated thereto said targeting species, or a different target species, preferably an antibody, characteristic of the biological cells and viruses to be detected.

A specimen which may comprise a RS virus related biological cell including a virus of types to be detected is in one embodiment exposed to an extended solid phase component which is coated at least in one location with a targeting species which will form complexes with the antigens of the biological cells and vira to be detected.

The extended solid phase is in one embodiment separated from the specimen, such as by washing the specimen off the extended solid phase, and the separated extended solid phase is then contacted with a mobile solid phase of dispersed polymeric carrier molecules according to the invention comprising the same or different targeting species, preferably an antibody. If immuno-complexes of antigens of biological cells including vira to be detected ("target" biological cells and "target" vira, respectively) have formed on the extended solid phase, the polymeric carrier molecules according to the invention will be bound to such complexes.

The unbound polymeric carrier molecules according to the invention of the mobile solid phase then are removed, such as by washing, and the extended solid phase is examined to determine the presence of polymeric carrier molecules according to the invention bound to the extended solid phase These may be visually detected in some cases, for example when the polymeric carrier molecules according to the invention have been initially stained or dyed. Microscopic examination may be employed. The use of tracers or labels for the polymeric carrier molecules according to the invention enables the use of other detection methods as described herein below in more detail.

By this means, the presence or absence of bound polymeric carrier molecules according to the invention enables detection of the presence or absence of the target biological cells including vira, and an evaluation of the quantity of bound polymeric carrier molecules according to the invention enables determination of the quantity of biological cells including vira in the specimen, for example by comparison with standard results for the assay of known samples.

The extended solid phase used in the present invention may be employed in a variety of forms or structures. The solid phase has a location where a targeting species, preferably an antibody, can bind or associate, and the formation of such a solid phase with said targeting species, preferably an antibody, enables contacting a specimen and other materials used in the method of the invention. Preferred specimens are body fluid samples as described in more detail herein below.

The extended solid phase is best formed in a way which enables simple manipulation for easy contact with the specimen and other reagents, for this purpose, the extended solid phase may form at least part of a dipstick, syringe, tube or container.

The specimen and other reagents can be drawn in and ejected from a syringe, caused to flow through a tube, or deposited in a container such as a test tube shaped container. In such devices, the extended solid phase can form the whole of the device, or part of it, where, in the case of a syringe, tube or container, the part formed of the extended solid phase will at least be exposed at the inside of the device to permit contact with specimen and reagents. Targeting species, preferably an antibody, is preferably concentrated at one location of the extended phase, to be exposed to the specimen.

One more preferred form of the extended solid phase is a dipstick. In such a dipstick, it is further preferred that the extended solid phase should be included at at least one end, and that the targeting species, preferably an antibody, conjugated on the extended solid phase should be concentrated at the end of the dipstick. The extended solid phase can however comprise the entire dipstick, with the targeting species, preferably an antibody, concentrated at one end, or in more than one location.

The dipstick may be entirely formed from the extended solid phase, at one end of which has been conjugated a coating of targeting species, preferably an antibody. In another embodiment the dipstick has an extended solid phase one end of which is adhered to a body portion. A coating of targeting species, preferably an antibody, is conjugated to the extended solid phase. In yet another embodiment the extended solid phase entirely forms a tubular container into which a specimen can be placed. Coatings of targeting species, preferably an antibody, are located near the bottom of the container and are concentrated in one or more locations.

The extended solid phase is composed of any material onto which the desired targeting species, preferably an antibody, can be effectively bound. For covalent binding with antibody protein, the solid phase material can be chosen to contain a functional carboxyl surface, with use of a water-soluble carbodilmide as a conjugation reagent. A preferred material is acrylic resin which has a carboxylated surface that enables, binding the desired targeting species, preferably an antibody, by conjugation For materials with amino surface groups, reactive carboxyl intermediates can be prepared by reacting with succinic anhydride. A variety of inorganic supports, typically glass, can also be prepared for covalent coupling with targeting species, preferably an antibody. Reference is made, for example to "Enzymology, A Series of Textbooks and Monographs," Vol. 1, Chapter 1, 1975, the disclosure of which is incorporated herein by reference.

Extended solid phase materials capable of binding targeting species, preferably an antibody, are selected from materials which do not cause serious interference with the assay steps.

The presence of non-specific agglutinators in a tissue specimen, particularly those coupled to immunoglobulins, can result in error by causing the binding of mobile polymeric carrier molecules according to the invention to the extended solid phase even in the absence of specific Ag. Repeated washes during the assay would reduce the non-specific binding, but removal of the non-specific agglutinators is necessary in order to avoid such undesired binding. A simple polystyrene latex surface, for example, can passively delete some of the agglutinators, whereas an Ig G-coated surface provides a better affinity.

For convenience in the following description, the extended solid phase will be referred to as the preferred dipstick, although other forms may be used as explained herein above.

In one embodiment the RS virus related biological cell essentially consists of or comprises a viral particle. A typical viral particle has an envelope of many, usually over one hundred, identical antigenic epitopes or protein sets. The proteins provide very strong binding with specific antibodies and form multiple conjugates or immune complexes Highly specific antibodies in monoclonal form are also available, either produced by hybridoma for the selected monoclonal mouse antibody, or by the human B-lymphocytes transformed by the Epstein-Barr virus for the human IgM.

When properly chosen, these monoclonal antibodies can provide consistent and reproducible binding with virions. With a proper supply of specific antibody, the present direct binding immunoassay, in contradistinction with competitive binding immunoassay practiced in radioimmunoassay, can be a reliable and very rapid procedure since the incubation time for a kinematic equilibrium needed in competitive binding assays is not presently required.

In accordance with the method of the present invention. antiviral antibody targeting species, either from the usual Ig fraction of the antisera or from monoclonal antibodies, is conjugated respectively with a solid phase dip stick as well as with a mobile solid phase, or the so called "monodispersed" polymeric carrier molecules according to the invention.

The functions of the dip stick are for the handling and the separation of bound from free antigens, whereas that of the mobile polymeric carrier molecules according to the invention are for the detection of the formed immuno-complexes. Coupling techniques between the antibody protein and various solid phase materials are well developed (see, for example, the above-mentioned W. J. Dreyer, U.S. Pat. No. 3,853.987).

In one embodiment of the method of the present invention described above, the resulting immunocomplex is a multi-layered "sandwich" comprising;

Dip stick+targeting species, preferably an antibody+viral antigen+targeting species, preferably an antibody+polymeric carrier molecule comprising a labelling species.

The amount of antibody required for covalent binding, however, can be less than a thousand times that of passive adsorption to a plastic such as polyvinyl chloride and the economics of using such an amount of highly specific targeting species, preferably an antibody, can be prohibitive.

An alternative way of binding that retains some strength of the covalent binding as well as the specificity of targeting species, preferably an antibody, is to bridge the targeting species and the solid phase with a first antibody, an anti-species antibody targeted against the Fc portion of the targeting antibody. Such an Fc portion is illustrated e.g. in "Immunology" (1981), The Upjohn Company, Kalamazoo, Mich.

That is, an inexpensive first antibody may initially be covalently bound to the solid phase, and the bound first antibody attracts the species-specific Fc portion of a targeting antibody, leaving the functional epitope of the targeting antibody unaltered with regard to an antigen of a RS virus related biological cell or a viral particle. Bridged with such a first antispecies antibody, the immunoassay of the present invention brings about the following coupling "sandwich" in the case of detection of a viral species;

Dip Stick+antispecies antibody+targeting antibody+viral antigen+targeting antibody+antispecies antibody+polymeric carrier molecule comprising a labelling species.

In the direct binding assay of the present invention, the couplings between the dipstick and targeting species, preferably an antibody, as well as the couplings between the polymeric carrier molecules according to the invention and targeting species, preferably an antibody, are prepared in advance, and elements of non-specific agglutination in the fluid specimen are removed or deactivated for pretreatment prior to the direct binding assaying as mentioned above.

The assaying procedure according to one embodiment of the invention is therefore simplified to the following steps:

(1) Insert the dipstick into an optionally pretreated specimen in the form of a body fluid sample.

(2) Incubate dipstick and sample.

(2) Wash the dipstick.

(3) Insert the dipstick into a dispersion of polymeric carrier molecules comprising at least one targeting species, preferably an antibody, and at least one labelling species, unless the polymeric carrier molecules have previously been added to the specimen.

(4) Optionally wash the preparation obtained under (3).

(5) Detect the polymeric carrier molecules according to the invention on the dipstick by detecting either the targeting species or the labelling species.

In order to use a minimal amount of wet chemistry, the present detection of attached polymeric carrier molecules according to the invention on a dip stick is made independent of the immune chemistry. By concentration of the targeting species, preferably an antibody, at one end of the dipstick, the bound polymeric carrier molecules according to the invention are concentrated at one location, which simplifies detection.

The polymeric carrier molecules according to the invention can include any dye or fluorescent compound for direct visual observation, or have metal elements or iron oxide doped or entrapped within in order to provide X-ray fluorescent or electromagnetic signals. Enzymatic amplification can also be designed into the polymeric carrier molecules according to the invention.

In one embodiment, the present method employs a direct binding assay instead of a competitive binding assay where a dynamic equilibrium necessitates lengthy incubation. The disclosed method can, of course, be employed in a competitive protein binding assay as well. The roles of the immune analytes antibody and antigen can also be interchanged, still making use of the immobilized solid phase for the signal amplification. Binding of antibody or various antigen molecules to the solid phase matter is well Known, in passive adsorption as well as in covalent coupling.

In the immunoassay of the present invention, the antigen characteristic for a RS virus related biological cell or a virus, which optionally appears in high multiplicity, is used as a bridge to connect the mobile and the immobilized solid phases. This connection can obviously also be served by various other antigens with multiple antibody binding sites. In cases of certain antigen without repetitive binding sites which cannot specifically connect more than one monoclonal antibody, polyvalent antibodies may also be used instead.

The method of the invention can also be designed to assay several analytes in a single procedure where each analyte is represented by a particular pair of corresponding binding partners including antibodies, antigens, and the same or different polymeric carrier molecules comprising one or more targeting species.

Detection of different types of RS virus related biological cells including virus can be done in accordance with the invention by conjugating a plurality of different targeting species, preferably an antibody, proteins capable of forming complexes with corresponding antigens of different biological cells including vira, respectively to the extended solid phase and to the mobile solid phase. The visual observation or other detection of any bound microspheres following the assay indicates that one or more of the different biological cells including vira is present in the specimen, and this assay, if positive, can be followed by assays for individual biological cells including vira of the different ones which were tested for simultaneously.

In another embodiment, the different RS virus related biological cells including virus can be both simultaneously and individually detected. For such a test, the different targeting species, preferably an antibody, corresponding to the antigens of a plurality of different types of biological cells including vira are conjugated to microspheres which are correspondingly labelled with different metal elements.

When more than one type of the differently labelled microspheres are bound to the extended solid phase in the assay of the invention, they may be separately and simultaneously detected. In this way, the presence of corresponding individual types of biological cells including vira in the specimen are simultaneously and separately detected. This is particularly relevant when determining subtypes of a respiratory syncytial virus.

The extended solid phase and the dispersed microspheres which are conjugated with targeting species, preferably an antibody, prepared as described above as individual components useful for the assay method of the invention, can be provided in the form of a virus detection kit comprising such components. Different kits may be provided, which differ as to the targeting species, preferably an antibody, coatings, and thus as to the vira to be detected.

Such a kit may further include as an individual component, a latex solid phase for removing non-specific agglutinators from a specimen prior to the assay. The preferred latex for this purpose is polystyrene coated with gamma immunoglobulin.

The extended solid phase and mobile solid phase components of the kit of the invention may be provided with targeting species, preferably an antibody, bound to an anti-species antibody as disclosed above. Also as disclosed above, the microsphere component may be labelled, and the extended solid phase can take the form of part or all of a dipstick, syringe, tube or container, coated with targeting species, preferably an antibody, in at least one location, as disclosed.

Furthermore, the extended solid phase component may be provided with a plurality of different targeting species, preferably an antibody, capable of forming complexes with corresponding antigens of different types of biological cells including vira. When it is so provided, the individual mobile solid phase component can be provided either to have the same plurality of targeting species, preferably an antibody, conjugated to each of the polymeric carrier molecules thereof, or a mixture of different types polymeric carrier molecules can be provided, each type having conjugated thereto a different targeting species, preferably an antibody, of said plurality, or in a further variation, the mobile solid phase component can be provided in the form of separate batches of polymeric carrier molecules, each batch having conjugated thereto a different targeting species, preferably an antibody, of said plurality.

Although it is preferred to use a polymeric carrier molecule comprising a targeting species and a labelling species as described herein above, the invention can also be exercised by using spherical particles including microspheres comprising a targeting species and optionally also a labelling species. Such microspheres may in particular be used in connection with a micro system comprising the kit according to the invention.

The kit according to the invention may also be applied in a micro system, such as a micro flow system described in WO 98/10267, one such system being marketed by Torsana Bio-sensor A/S, Denmark.

The principle behind the technology of a micro flow system is that by controlling the flow rate of at least two guiding streams, a sample stream can be accurately positioned on a target surface.

By controlling the flow ratios between the guiding streams and the sample stream, the sample stream can be focused to a width of a few mm. The sample stream carries the molecules to interact with the surface.

Immobilized lanes of the system are interacted with liquid streams containing unknown samples in the y-dimension.

Thousands of unique intersection points are created where reaction can occur.

The fact that no turbulence occurs in very narrow fluid streams results in diffusion being the only phenomena perturbing the focus of the sample stream. In effect, the technology permits the precise positioning of a liquid stream on a planar surface In this way it is possible to position material with a precision of a few mm.

The microfluidic system allows for control of very narrow streams of liquid carrying the material (DNA, proteins, cells) to be interacted with the surface of the chip.

The micro flow system enables immobilization of reactant streams, in the present context streams of conjugate comprising the polymeric carrier and subsequent testing with one or several samples creating a weave with thousands of intersection points where chemical reactions occur and are detected. The entire procedure is performed in a closed fluidic system providing the flexibility in terms of sample— and reactant application, choice of immobilization—and detection chemistries, and array layout.

In particular when using the kit for testing for a plurality of biological cells and/or inflammatory indicators, such as providing profiles of inflammatory indicators, the invention suitably includes the use of the kit in a microsystem.

In addition to micro systems, the kit according to the invention may also form part of a conventional macro system such as e.g. a lateral flow device. Examples of such devices are listed herein below.

U.S. Pat. No. 5,610,077 (Unilever) discloses a process for performing a specific binding assay. Accordingly, there is provided a method according to the invention for carrying out a specific binding assay comprising the steps of reacting (a) a sample under assay comprising a RS virus related biological cell with (b) a specific binding partner for the RS virus related biological cell being tested for, including a polymeric carrier molecule according to the invention, immobilised on a solid support, and (c) a specific binding partner for the RS virus related biological cell being tested for, including a polymeric carrier molecule according to the invention, which is conjugated to a detectable marker, thereby to form a sandwich complex by reaction between whatever quantities are present of the RS virus related biological cell being tested for with reagents (b) and (c) and immobilising the marker to the support via the RS virus related biological cell being tested for the marker being detected or assayed as an index of the quantity of the RS virus related biological cell being tested for present in the sample (a), the improvement which comprises using reagents (b) and (c) together for reaction with sample (a) and avoiding competitive interference between the binding reactions of the RS virus related biological cell being tested for and reagents (b) and (c) by using as reagents (b) and (c), monoclonal antibodies each of narrow and different, non-interfering specificity, the binding reagent (b) being immobilised on the surface of a displacer body which occupies a majority of the volume of a well or cup containing aqueous liquid in which the specific binding reaction takes place.

The narrow specificity required of the antibody is a-capacity to bind specifically with the RS virus related biological cell under test but without preventing the binding reaction between the RS virus related biological cell under test updates other specific binding partner. The conjugate between antibody and the enzyme or other marker, and/or the antibody (if any) which is coupled to the solid surface, may comprise a monoclonal antibody or other antibody of sufficiently narrow specificity to ensure that the desired assay reaction or reactions are not impeded by competition between the conjugate and the immunosorbent in their reactions with whatever quantities are present of the RS virus related biological cell being tested for in the sample under assay. An antibody of sufficiently narrow specificity may also be obtained in the (polyclonal) immunoglobulins of antisera raised against discrete chemical or physical molecular fragments of the material under test, for example, antibody against Fc fragments (or against smaller peptide fragments) of immunoglobulins to be tested for, or against sub-units or peptides of protein antigens to be tested for. The object in each case is to ensure substantial freedom from interference which can arise particularly, for example, in carrying out immunoassays of the "sandwich" or "antiglobulin" test configurations.

In a "sandwich" test configuration, antigen under test can be specifically adsorbed to a first antibody bound to a solid surface, and a second antibody carrying an enzymic or other (e.g. fluorescent or radioactive) marker is specifically bound to the adsorbed antigen under test. Marker specifically so bound is used for measurement and determination of the antigen under test, e.g. by direct measurement, such as radiometry or fluourometry, or exposure of enzyme marker to substrate followed by product measurement. Thus, in preferred sandwich tests, the two antibodies used can have different, non-interfering specificity with respect to the same antigen under test.

In an "antiglobulin" test configuration, sometimes also referred to as a "sandwich" test configuration, the position is analogous; the material under test is itself an immunoglobulin; the material bound to a solid surface is its corresponding antigen or hapten; and the material carrying the marker is an antiglobulin corresponding to the species and immunoglobulin type of the antibody under test. In preferred antiglobulin tests, the antiglobulin can have sufficiently narrow specificity as not to interfere with the subsequent adsorption of its corresponding globulin to the insolubilised antigen.

If antibodies from ordinary antisera raised against unmodified antigen (polyclonal antibodies) are used in sandwich or antiglobulin tests, there is a very likely risk that if all ingredients are mixed in a single step there will be interference between the two specific adsorption reactions. When such tests are carried out according to the present invention, using apparatus as described herein, such interference can be avoided either by using antibodies of narrow specificity as described, or else by ensuring that the binding of test material to the solid surface takes place before exposure of test material to the other (marker-conjugated) binding agent if there is a risk that binding by that other agent would prevent subsequent adsorption to the solid surface. Such a sequence can be ensured by arranging for slow release of the other (marker-conjugated) binding agent.

Particular instances of suitable assay specificities, antibody specificities, and slow-release forms of conjugated reagent (c) are described for example below.

It has also been found that in carrying out such specific binding assays, a worthwhile improvement in reaction kinetics can be obtained if the reaction liquid containing ingredients (a), (b) and (c) is contained in a well or cup of which the majority of the volume is occupied by a displacer body. (The use of inserts of various rod or ball shaped forms is known in connection with other kinds of immunoassay, as described in G. B. Specification Nos. 1,414,479 and 1,485,729.)

The displacer body can, for example, be of a shape substantially complementary to and slightly smaller than that of the cup or well, so that the liquid phase containing one of the specific binding reagents is approximately in the form of a shell occupying the space between the displacer and the cup or well. The displacer can be loose-fitting and not fixedly mounted. i.e. movable relatively to the cup or well, so that by relative motion between displacer and well the liquid between them can be given a stirring or agitation motion.

For example, a round well can have a round displacer therein with an external diameter slightly smaller than the diameter of the well. The presence of the displacer can reduce the space available for liquid in the well by a factor of for example 214 10, e.g. 3–8, comparing volumes based on similar liquid levels in the well, e.g. when filled to its normal operating level, or its maximum capacity. For example, a microliter well designed to have 300 microliter of liquid filled into it during a normal assay, can be used with a displacer leaving 30–150 microliter liquid space. e.g 50–100 microliter.

The use of wells or cups together with displacers as described herein can improve the efficiency of the assay reaction steps because, in the first place, it allows more concentrated reagents to be used with no increase in the weight of reagent or decrease in the size of the microliter wells, compared with the normal conditions encountered in microliter wells of given size, and in the second place, it increases the sensitised surface area available to react with a given liquid reagent volume, so that comparatively faster adsorption kinetics can be achieved without having to increase specific reagent density on the sensitised surface or encountering problems of crowding.

A set of displacer bodies can be preferably present in certain embodiments of the invention, e.g. as an integral part of a lid which can be fitted onto a microliter plate, e.g. a standard plate of 8 times 12 wells. The set can be large enough to fit all wells of the plate or a sub-set thereof, e.g. a row. The dimensions of the displacers and the volume of liquid to be dispensed into the well can be chosen relative to the well in the manner described above, and preferably so that the liquid to be tested is in contact with substantially the major part and preferably the whole inner surface of the well.

The immobilised specific binding partner (reagent (b) for the RS virus related biological cell to be assayed can be immobilised on the wall of the well or cup in which the assay reaction takes place. Alternatively, according to a feature of the invention independently capable of providing advantage and convenience in use, a liquid displacer, for example in the form of a stick, peg or stud, for dipping into a liquid assay reagent, can have an immunosorbent surface. This allows the portion of the assay materials needing to be carried over from one reagent to the next, and the associated manipulations to be handled more easily than when the sensitised surface is part of a hollow well. An alternative form for such a liquid displacer body is a tuft of bristles or leaves of suitable material, or equivalent body with large surface area. A further alternative form is a stud or peg with relatively hollowed-out and projecting portions of its surface, e.g. with grooves and associated ribs, e.g. annular grooves. Such an arrangement can give robustness, increased sensitised surface area, and better reactivity.

Test apparatus according to related embodiments of the invention can thus comprise a set of sensitised liquid-displacer bodies of one or more of such forms, joined to a common handling-bar, link or lid, and for use in combination with a complementary set or sets of wells containing any of the remaining materials used in the assay. The several displacer bodies of the set can have the same or different sensitisation so that one or a plurality of different assay types can be carried through simultaneously. If desired, the displacer bodies can be removably and exchangeably mounted on the handling bar, link, or lid, so that sets of desired specificity can be built up at will from a common stock for carrying out large numbers of tests according to a desired pattern.

One advantage of such arrangements is that a number of displacer bodies can be sensitised in the same body of liquid regent, avoiding fluctuating conditions of concentration, etc., resulting from dosing aliquots into wells.

The displacer bodies can, in this embodiment, be of any material suitable for the preparation of an immunosorbent by covalent bonding or adsorption: e.g. polystyrene, nylon, or cellulose acetate. (The nature of the displacer surface does not matter provided it is inert, when the sensitisation is to be on the well surface rather than the displacer surface.) Linkage of antibodies, antigens, etc., to the displacer bodies can be carried out by linking methods known in themselves, e.g. partial acid hydrolysis of nylon surface, substitution of exposed amine surface with glutaraldehyde, and coupling of material to be bound, e.g. antibody or antigen to immobilised aldehyde groups. Suitable methods among a wide variety are given for example by Inman & Hornby (1972) Biochem. J. 129, 255, Campbell, Hornby & Morris (1975) Biochim. Biophys. Acta 384, 307; Mattiasson & Nilsson (1977) F.E.B.S. Letters 78, 251, and G.B. patent specifications Nos. 1,470,955 and 1,485,122.

It can be seen that the invention also provides a kit of test materials for carrying out a specific protein-binding assay, comprising (i) an immobilised specific binding partner for a RS virus related biological cell to be tested for, including a polymeric carrier molecule according to the invention, carried on a solid support, and (ii) a marker-conjugated specific binding partner for the RS virus related biological cell to be tested for, including a polymeric carrier molecule according to the invention which can be added to a reaction liquid contacting immobilised reagent (i) either as a slow-release form, or in any form provided that the specific binding partners in reagents (i) and (ii) include an antibody of narrow specificity so that reagents (i) and (ii) do not interfere with each other's binding reactions with the RS virus related biological cell to be tested. Optionally the kit can also comprise materials for later estimation of the amount of marker immobilised during the assay.

Reagent (i) can be immobilised on either a displacer body for a reaction well, or on a reaction well wall, as described above. A slow-release form of reagent (ii) can be for example a sucrose or equivalent glaze on a complementary surface of either the displacer or the well wall, also as described above The narrow-specificity antibody can be selected for example from monoclonal antibodies in the manner already described.

U.S. Pat. No. 5,501,949 (Murex) pertains to a method for detection or quantitation of an analyte in a solution. Accordingly, the present invention in one embodiment pertains to a method comprising the steps of:

(a) contacting the solution with insoluble particles or a polymeric carrier molecule according to the invention having attached thereto a binding component specific for the analyte, so as to form a suspension comprising a first complex wherein the first complex comprises the analyte, the binding component and the insoluble particle;

(b) applying the suspension to at least a portion of a semi-permeable membrane having interstices of dimensions relative to the insoluble particles or the polymeric carrier molecules according to the invention and having a thickness such that the insoluble particles or the polymeric carrier molecules according to the invention are retained throughout the thickness of the semi-permeable membrane, the portion of the semi-permeable membrane retaining the particles or polymeric carrier molecules defining an assay zone;

(c) contacting the semi-permeable membrane containing the assay zone with a labeling component, preferably comprised in a particle or a polymeric carrier molecule according to the invention and forming part thereof, said particle or polymeric carrier molecule being capable of specifically binding to the first complex so as to form a second complex wherein the second complex comprises the first complex including the labeling component, wherein the semi-permeable membrane permits the labeling component which is not bound to the first complex to pass out of the assay zone; and (d) measuring the signal produced by the labeling component of the second complex as an indicator of the presence or amount of the analyte present in the solution.

U.S. Pat. No. 5,155,021 (EASTMAN KODAK) discloses a diagnostic kit useful for the determination of a herpes simplex virus. Accordingly, the present invention in one embodiment relates to a diagnostic kit comprising:

i) polymeric particles Which are substantially free of chemical or biological materials, having an average diameter of from about 0.01 to about 10 micrometers, and which have a surface area of from about 0.1 to about 600 $m^2/g$ of particles, which particles are capable of having herpes simplex viral antigen directly bound thereto, ii) a disposable test device comprising a microporous membrane which has an average pore size of from about 0.1 to about 20 $\mu$m, and iii) antibodies which bind to a RS virus related biological cell according to the invention.

The antibodies may be labeled with enzyme or they may be unlabeled, in which case the kit further comprises labeled antibodies which bind to said biological cell. Test device comprises three test wells, each well having a microporous membrane prepared from a polyamide mounted therein. Polymeric particles are supplied on the microporous membrane of said test device—particles are supplied in an aqueous suspension. The microporous membrane may be any suitable membrane, for example selected among the following commercially available pads Whatman GF/D
Whatman F147-11
Whatman GF/AVA
Whatman 147-02
Whatman GF/DFA
Whatman F147-09
Whatman F075-17*
Millipore Rapid Q24*
Millipore Rapid Q27
Ahlstrom A142

Furthermore, an absorbant pad may be provided to absorb the liquid from the aqueous suspension. Absorbant pads are for example Whatman D28
Whatman 1.5WF*
Whatman 3 MM CHR Further examples of assay devices and diagnostic methods pertaining to the invention includes, but are not limited to:

An assay device preferably comprising:

i) a zone for applying a body fluid sample comprising an indicator of RS virus infection, said zone comprising at least one movable reporter species capable of binding said indicator, said application zone being in liquid contact with ii) a zone for detecting the presence, amount or concentration of said at least one reporter species bound to said indicator, said zone further comprising a binding species for immobilizing onto said detection zone at least a substantial amount of said indicator comprised in said body fluid sample, and optionally iii) a positive control zone generating a positive control confirming the transfer of at least part of said body fluid sample from said application zone to said detection zone.

The at least one reporter species comprised in the sample application area preferably comprises an antibody comprising at least one tag, linker or marker that makes it possible at least to detect the presence of said marker, and preferably also makes it possible to quantifiably detect said antibody and/or said reporter species bound to said indicator.

The binding species of the detection zone is preferably also an antibody, but this antibody may not comprise any tag, label or marker. It is thus possible to immobilise onto the detection zone an amount of a quantifiably detectable reporter species that accurately reflects the amount of marker present in the body fluid sample. The at least one tag, label or marker used preferably allows both visual detection, by means of the generation of e.g. electromagnetic radiation or a visible colour, and quantification of e.g. the emitted electromagnetic radiation.

Movable reporter species shall be understood to comprise a reporter species capable of moving on e.g. a solid or semi-solid surface, e.g. when being applied to a lateral flow device.

In one embodiment of this aspect of the invention there is provided an assay device for detecting an indicator of RS virus infection present in a body fluid sample, said device comprising:

i) a hollow casing having a body fluid sample application aperture and a test result observation aperture, ii) a bibulous body fluid sample receiving member within said hollow casing to receive said body fluid sample applied to said sample application aperture, iii) a test strip comprising a dry porous carrier such as nitrocellulose within said casing and extending from said bibulous body fluid sample receiving member to and beyond said test result observation aperture, said dry porous carrier having a test result zone observable through said observation aperture, iv) at least one of said bibulous body fluid sample receiving member and said test strip containing upstream from said test result zone a detectable reporter species capable of specifically binding said indicator to form a first complex, v) said reporter species comprising at least one particulate label, such as a dye sol, a metallic sol or a coloured latex particle, and optionally also at least one fluorescently detectable label, said label being released into a mobile form by said body fluid sample, wherein mobility of said label within said test strip is facilitated by either coating at least a portion of said test strip upstream from said test result zone with a material comprising a polysaccharide, or drying said label onto a portion of said test strip upstream from said test result zone in the presence of a material comprising a polysaccharide, in an amount effective to reduce interaction between said test strip and said label, and wherein said dry porous carrier contains in said test result zone a means for binding said first complex, said means for binding comprising specific binding means immobilized in said test result zone, and wherein migration of said body fluid sample from said bibulous sample receiving member into and through said dry porous carrier conveying by capillarity said first complex to said test result zone of said dry porous carrier whereat said binding means binds said first complex thereby to form a second complex, and vi) determining the presence, amount or concentration of said second complex being observable through said test result observation aperture.

In another embodiment there is provided an assay device for detecting an indicator of RS virus infection in a body fluid sample, said device comprising a solid support including at least one detectable reporter species on a test area of the solid support, said at least one detectable reporter species being capable of binding said marker, said reporter species further comprising a liposome or a microcapsule comprising a visible particulate dye compound and optionally also a fluorescently detectable marker.

In yet another embodiment there is provided an assay device comprising i) a sample application area comprising a predetermined amount of a reporter species comprising an antibody capable of binding said indicator deposited thereon, said area being in fluid communication with ii) a reaction zone comprising a mobilizable reporter species comprising an antibody capable of binding said indicator, said reporter species further comprising at least one visually detectable particle and/or at least one fluorescently detectable particle, and iii) a detection zone comprising a reporter species comprising an antibody capable of binding said indicator, wherein, when said body fluid sample comprising said indicator is applied to said sample application area, a threshold amount of the indicator is bound to said antibody and thereby prevented from binding to the antibody being present in the reaction zone, and wherein the indicator remaining unbound in said body fluid sample passes from the sample application area through said reaction zone, where it is bound to said mobilizable reporter species comprising i) an antibody capable of binding said indicator, and ii) at least one visually detectable particle and/or at least one fluorescently detectable particle, and wherein the indicator bound to the mobilizable reporter species is brought into contact with the detection zone, where the indicator is bound to said reporter species comprising said antibody capable of binding said indicator, and wherein said binding of said indicator results in immobilization of said mobilizable reporter species further comprising i) an antibody capable of binding said indicator, and ii) at least one visually detectable particle and/or at least one fluorescently detectable particle, The present invention is concerned with a method for detecting Respiratory syncytial virus (RS virus), or subtypes thereof, and a kit for use in such methods. The RS virus may be detected in any body fluid, including nasal secretions, and in the lung.

Two different subtypes of RSV (A and B) have been demonstrated for the first time in 1985 based on analyses of serologic antigenic variation using antibodies respectively directed against the large glycoprotein (G), fusion protein (F), matrix protein (M), nucleoprotein (NP) and phosphoprotein (P) components of the long strain of RS virus.

Subtype A viruses reacted with all the antibodies, whereas subtype B viruses showed different epitope characteristics in four structural components. The number of altered epitopes were 5/6, 1/2, 2/6 and 1/6 in the G. F, M and NP components, respectively (Mufson M A et al, *J. Gen Virol* 1985 Oct: 66 (ptIG):2111–24).

Peptides deduced from the central conserved region (residues 158 to 189) of the G protein of human respiratory syncytial virus (HRSV) subtypes A and B have been used as antigens in subtype-specific enzyme-linked immunosorbent assays (G-peptide ELISAs) (Langedijk, J P et al., *J Clin Microbiol* 1997 July p1656–1660.

All the above-mentioned antigenic determinants are suitable for detecting RS virus, or subtypes thereof, in accordance with the present invention.

A colorimetric microtiter plate (MTP) PCR system for specific detection of the respiratory syncytial virus (RS virus) nucleocapsid gene and differentiation of viral subtypes A and B has been developed for clinical laboratory diagnosis and simultaneous subgroup classification of RSV infection (Tang, Y W et al., *Diagn Microbiot Infect Dis* 1999 August; 34 (4) 333–7). Such a test may be used in combination with the present invention.

In one embodiment the present invention pertains to simultaneous and rapid detection of RSV and the prevailing subtype (A or B) by using a polymeric carrier molecule according to the present invention comprising at least one targeting species characteristic for RS virus, including any subtype thereof, and at least one labelling species. Such a rapid detection of RS virus in nasal secretion is novel and does not require expensive laboratory equipment and time-consuming procedures.

When the present invention pertains to detection of RS virus, the polymeric carrier molecule may comprise any targeting species including antibodies capable of detecting RS virus including any subtype thereof (A or B, or otherwise). Preferred targeting species comprise antibodies such as e.g. the highly variable attachment protein G has limited homology between HRSV subtypes (53% amino acid homology). However, within the subtypes the amino acid homology is much larger: >80% within HRSV subtype A (HRSV-A) strains and >90% within HRSV-B strains.

Accordingly, protein G is a good candidate antigen for a discriminatory assay. The ectodomain of protein G contains a central, conserved, relatively hydrophobic region bounded by two hydrophilic, polymeric mucin-like regions. It is a major antigenic site, and peptides corresponding to this region can be used as antigens in immunoassays and probably as well in the invention in question.

Preferred antibodies for detecting RS vira according to the invention are selected from the below indicated list according to one embodiment of the invention:

Commercially available antibodies against human RSV (HRSV) virus (including subtypes A and B) suitable for use in the present application are for example as follows:

| Polyclonal antibodies: | |
|---|---|
| Biodesign International | Goat anti RSV (RSV-A and RSV-B) Specific for all viral antigens of RSV-A and RSV-B |
| Biogenesis | Recognises most RSV antigens |
| Fitzgerald Industries Int. | Fitzgerald Human RSV isolate, confirmed. |
| Monoclonal antibodies: | |
| Biodesign International | Specific for the fusion protein of RSV, types A & B. |
| Biodesign International | Specific for the fusion protein (F1 subunit). |
| Biodesign International | Immunogen: Purified RSV virus, strain Long |
| Biodesign International | Specific for the nucleoprotein of RSV including RSV-A and RSV-B |
| Biogenesis | RSV; Fusion protein |
| Biogenesis | This pool of antibodies reacts with RSV fusion and attachment glycoproteins, phosphoprotein and M2 proteins |
| Biogenesis | Recognises human isolate, all RSV antigens |
| Biogenesis | Recognises RSV glycoprotein molecular weight 89kD |
| Biogenesis | Recognises a 41/44 kD nucleoprotein |
| Chemicon Int. | Mab 92-11C specific for HRSV-A fusion protein 1b, and Mab 102-10B specific for HRSV-B fusion protein 1c |
| Fitzgerald Industries Int. | Specific for the fusion protein of RSV |
| Fitzgerald Industries Int. | Specific for the nuclear protein of RSV |

In particular the following commercially available antibodies may be used:

| RSV specific Antibodies | |
|---|---|
| Biodesign Goat anti RSV (all antigens) | B65860F |
| Chemicon Mouse anti RSV Fusion Protein 1c | MAB8582 |
| Chemicon Mouse anti RSV Fusion Protein 1b | MAB8581 |
| Chemicon Mouse anti RSV, monoclonal | MAB858-4 |
| Chemicon Goat anti RSV, polyclonal | AB1128 |
| Virostat Goat anti RSV (all antigens) | 0601 * |
| Fitzgerald Goat anti RSV | 20-RG45 |
| Virostat Mouse anti RSV Fusion protein (F1 subunit) | 0621 |
| Virostat Mouse anti RSV Fusion protein | 0631 * |
| Serotec Mouse anti RSV Fusion protein | MCA490 |
| Virostat Mouse anti RSV Nucleoprotein | 0671 |
| Virostat Mouse anti RSV Protein G | 0691 |

The present invention employs targeting species, labelling species, and more generally molecular species. The term "molecular species" in the context of the present invention is used to denote, for example: molecules or ionic species which serve as labels or markers (such as enzymes, or fluorescent or luminescent species); or molecules which serve as targetting species, i.e. molecules which are capable of binding selectively or specifically to one or more target molecules, moieties, receptors or epitopes (examples of such targetting species being haptens or hapten conjugates, antigens, antibodies, nucleotide sequences and hormones). The invention in one particular embodiment relates to simultaneously or sequentially using any one or both of a first targeting species and a second targeting species including polyclonal and monoclonal antibodies that may be, respectively, i) identical or non-identical, and ii) specific for the same or different epitopes of antigenic determinants characteristic for a RS virus related biological cell according to the invention.

Molecular species according to the invention are to be found among numerous different types of substances, examples being: proteins, such as ferritin, phycoerythrins, phycocyanins or phycobilins; enzymes, such as horseradish peroxidase, alkaline phosphatase, glucose oxidases, galactosidases or ureases; toxins; drugs; dyes; fluorescent, luminescent, phosphorescent or other light-emitting substances; metal-chelating substances, such as iminodiacetic acid, ethylenediaminetetraacetic acid (EDTA), diethylenetriaminepentaacetic acid (DTPA) or desferrioxamine B; substances labelled with a radioactive isotope; or substances labelled with a heavy atom.

Many molecular species will be able to serve as labelling species in conjugates according to the invention. Additional examples of labelling species are listed herein immediately below.

i) Fluorescent substances selected from, e.g., fluorescein (suitably as fluorescein isothiocyanate, FITC), fluoresceinamine, 1-naphthol, 2-naphthol, eosin, erythrosin, morin, o-phenylenediamine, rhodamine and 8-anilino-1-naphthalenesulfonic acid.

ii) Radioactive isotopes of relevance may be selected, for example, among isotopes of hydrogen (i.e. tritium, $^3$H), carbon (Such as $^{14}$C), phosphorus (such as $^{32}$P), sulfur (such as $^{35}$S), iodine (such as $^{131}$I), bismuth (such as $^{212}$Bi), yttrium (such as $^{90}$Y), technetium (such as $^{99}$Tc), palladium (such as $^{109}$Pd) and samarium (such as $^{153}$Sm).

iii) Heavy atoms of relevance may be selected, for example, among Mn, Fe, Co, Ni, Cu, Zn, Ga, In, Ag, Au, Hg, I, Bi, Y, La, Ce, Eu and Gd. Gold (Au) may be used in combination with silver (Ag) as an enhancement reagent and Au is a particularly useful heavy atom in many cases.

Molecular species may also be in the form of targetting species capable of selectively binding to, or selectively reacting with, a complementary molecule or a complementary structural region of a material of biological origin, examples of relevant targetting species are, for example; antigens; haptens; monoclonal or polyclonal antibodies; gene probes; natural or synthetic oligo- or polynucleotides; certain natural or synthetic mono-, oligo- or polysaccharides: lectins: avidin or streptavidin; biotin; growth factors; hormones; receptor molecules: or protein A or protein G. For examples of appropriate antibodies, reference is made to the working examples given herein. Examples of relevant hormones may be selected from steroid hormones (e.g. estrogen, progesterone or cortisone), amino acid hormones (e.g. thyroxine) and peptide and protein hormones (e.g. vasopressin, bombesin, gastrin or insulin).

The present invention may in one embodiment employ standard immunohistochemical or cytochemical detection procedures for the detection of the predetermined RS virus related biological cell, or any suitable modifications of such procedures. Accordingly, the invention may employ any assay resulting in the recognition of an antigens determinant mediated by an immunochemical reaction of the antigenic determinant with a specific so-called primary antibody capable of reacting exclusively with the target antigenic determinant in the form of a predetermined RS virus related biological cell.

The primary antibody is preferably labelled with an appropriate label capable of generating—directly or indirectly—a detectable signal. The label is preferably an enzyme, an isotope, a fluorescent group or a heavy metal such as gold.

In another embodiment, the invention employ the detection of the primary antibody by immunochemical reaction with specific so-called secondary antibodies capable of reacting with the primary antibodies. In this case the secondary antibodies are preferably labelled with an appropriate label such as an enzyme, an isotope, a fluorescent group or a heavy metal such as gold.

In yet another embodiment, the present invention employs a so-called linker antibody as a means of detection of the predetermined RS virus related biological cell. This embodiment exploits that the immunochemical reaction between the target antigenic determinant in the form of the predetermined RS virus related biological cell and the primary antibody is mediated by another immunochemical reaction involving the specific linker antibody capable of reacting simultaneously with both the primary antibody as well as another antibody to which enzymes have been attached via an immunochemical reaction, or via covalent coupling and the like.

In yet another embodiment according to the present invention, the immunochemical reaction between a target antigenic determinant in the form of a predetermined RS virus related biological cell and the primary antibody, or alternatively, between the primary antibody and the secondary antibody, is detected by means of a binding of pairs of complementary molecules other than antigens and antibodies. A complementary pair such as e.g. biotin and streptavidin is preferred. In this embodiment, one member of the complementary pair is attached to the primary or secondary antibody, and the other member of the complementary pair is contacted by any suitable label such as e.g. an enzymes, an isotope, a fluorescent group or a heavy metal such as gold.

A sample potentially containing a predetermined RS virus related biological cell to be detected is preferably brought into contact with a polymeric carrier molecule comprising a labelled or non-labelled primary antibody capable of detecting said biological cell. The antibody becomes immunochemically bound to the predetermined RS virus related biological cell comprised in the sample. The RS virus related biological cell is then bound to a solid support containing the same or another labelled or non-labelled primary antibody capable of detecting said RS virus related biological cell. When a lateral flow device is used, the labelled antibody bound to the predetermined RS virus related biological cell is detected by reaction with appropriate reagents, depending on the choice of detection system.

The sample comprising the predetermined RS virus related biological cell to be detected and optionally also quantified is in one embodiment of the invention subjected to at least one of the detection reactions described below. The choice of detection reaction is influenced by the targetting species in question as well as by the labeling species it is decided to use.

When an enzyme label is used as a labelling species, the RS virus related biological cell bound to a solid support as described herein above is treated with a substrate, preferably a colour developing reagent. The enzyme reacts with the substrate, and this in turn leads to the formation of a coloured, insoluble deposit at and around the location of the enzyme. The formation of a colour reaction is a positive indication of the presence of the RS virus related biological cell in the sample.

When a heavy metal label such as gold is used, the sample is preferably treated with a so-called enhancer in the form of a reagent containing e.g. silver or a similar contrasting indicator. Silver metal is preferably precipitated as a black deposit at and around the location of the gold. When a fluorescent label is used, a developing reagent is normally not needed.

It may be desirable to introduce at least one washing step after which some of the constituents of the sample are preferably coloured by reaction with a suitable dye resulting in a desirable contrast to the colour provided by the labelling species in question. After an optional final washing step, the specimen is preferably coated with a transparent reagent to ensure a permanent record for the examination.

Detection of the labelling species in question preferably indicates both the localization and the amount of the target antigenic determinant in the form of the predetermined RS virus related biological cell. The detection may be performed by visual inspection, by light microscopic examination in the case of enzyme labels, by light or electron microscopic examination in the case of heavy metal labels, by fluorescence microscopic examination, using irradiated light of a suitable wavelength in the case of fluorescent labels, and by autoradiography in the case of an isotope label. Detection of the presence of the RS virus related biological cell—and preferably also the amount of the cell—by visual inspection of the sample is preferred.

In a particularly preferred embodiment, the visual detection is based on a cut-off point above which one colour indicates the presence of the RS virus related biological cell above a certain minimum amount (cut-off point), and below which cut-off point another colour indicates that the RS virus related biological cell is present in an amount of less than that indicated by the cut-off point. When fluorescent markers are used the amounts of biological cell detected is directly correlatable with the fluorescence measured by a detection unit.

Enzyme-Linked Immuno-Sorbent Assays (ELISA) in which the RS virus related biological cell is detected directly, initially by detection by a targeting species in the form of an antigen, hapten or antibody, and subsequently by means of an enzyme which is linked such as covalently coupled or conjugated either—when an antigen or hapten is to be determined—to an antibody which is specific for the antigen or hapten in question, or—when an antibody is to be determined—to an antibody which is specific for the antibody in question—are particularly preferred for detecting the predetermined RS virus related biological cell according to the present invention.

In one preferred embodiment, the predetermined RS virus related biological cell to be detected is bound or immobilized by immunochemically contacting the cell with a so-called "catching" antibody attached by e.g. non-covalent adsorption to the surface of an appropriate material such as a solid support. Examples of such solid support materials are polymers such as e.g. nitrocellulose or polystyrene, optionally in the form of a stick, a test strip, a bead or a microtiter tray.

Commercially available nitrocellulose membranes are for example
   Millipore Hi-Flow Plus HF07504
   Millipore Hi-Flow Plus HF09004
   Millipore Hi-Flow Plus HF12004
   Millipore Hi-Flow Plus HF13504
   Millipore Hi-Flow Plus HF18004
   Sartorius Unisart CN40
   Sartorius Unisart CN90
   Sartorius Unisart CN200*

A suitable enzyme-linked specific antibody is allowed to bind to the immobilized biological cell to be directly detected. The amount of bound specific antibody, i.e. a parameter that is correlatable to the immobilized cell, is determined by adding a substance capable of acting as a substrate for the linked enzyme. Enzymatic catalysis of the substrate results in the development of a detectable signal such as e.g. a characteristic colour or a source of electromagnetic radiation. The intensity of the emitted radiation can be measured e.g by spectrophotometry, by colorimetry, or by comparimetry. The determined intensity of the emitted radiation is correlatable—and preferably proportional—to the quantity of the predetermined RS virus related biological cell to be detected. Examples of preferred enzymes for use in assays of this type are e.g. peroxidases such as horseradish peroxidase, alkaline phosphatase, glucose oxidases, galactosidases and ureases.

Immunochemical assays of a type analogous to ELISA, but employing other means of detection, are also suitable for detecting directly a RS virus related biological cell according to the present invention. Such assays are typically based on the use of specific antibodies to which fluorescent or luminescent labelling species are covalently attached. So-called "time-resolved fluorescence" assays are particularly preferred and typically employ an europium ion label or an europium chelator, even though certain other lanthanide species or lanthanide chelators may also be employed. In contrast to many traditional fluorescent labelling species the fluorescence lifetime of lanthanide chelates is generally in the range of 100–1000 microseconds. In comparison, fluorescein has a fluorescence lifetime of only about 100 nanoseconds or less. By making use of a pulsed light source and a time-gated fluorometer, the fluorescence of lanthanide chelate compounds can be measured in a time-window of about 200–600 microseconds after each excitation. A main advantage of this technique is the reduction of background signals which may arise from more short-lived fluorescence of other substances present in the analysis sample or in the measurement system.

Additional assays employing immunochemical detection techniques capable of being exploited in the present invention belong to the group of "immunoblotting" procedures, such as e.g. "dot blot" and "western blot" procedures. In the western blot procedure, which is typically employed for the analysis and identification of antigenic polypeptides or proteins, the predetermined RS virus related biological cell of interest is preferably transferred or fixed to a solid support or a membrane sheet such as e.g. a sheet of nitrocellulose or chemically treated paper to which the RS virus related biological cell is capable of binding. Binding may be mediated by a targeting species such as e.g. an antibody bound to the support. An appropriate targeting species in the form of a specific antibody is initially added and later followed by a labelled second antibody against the first antibody. Labelled protein-A may be added as an alternative to the addition of labelled second antibody The label is preferably a radioisotope, a fluorescent dye, an enzyme or a heavy metal such as gold or a colloid thereof. The presence and location of the RS virus related biological cell is detected in an appropriate manner as described herein above.

"Connecting moiety" as used herein denotes any chemical species capable of forming a conjugate by binding a molecular species and a polymeric carrier molecule. The establishment, on the polymeric carrier molecule, of covalently bound reactive moieties deriving from divinyl sulfone, and the establishment of covalent bonds between, on the one hand, such moieties, and, on the other hand, molecular species as defined herein, are particularly preferred according to one embodiment of the invention.

Additional examples of connecting moieties, or reactive, functional groups, are chemical species comprising as a reactive group compounds such as e.g. 4-fluoro-3-nitrophenyl azide, acyl azides such as benzoyl azide and p-methylbenzoyl azide, azido formates such as ethyl azidoformate, phenyl azidoformate, sulfonyl azides such as benzenesulfonyl azide, phosphoryl azides such as diphenyl phosphoryl azide and diethyl phosphoryl azide, diazo compounds such as diazoacetophenone and 1-trifluoromethyl-1-diazo-2-pentanone, diazoacetates such as t-butyl diazoacetate and phenyl diazoacetate, beta-keto-alpha-diazoacetates such as t-butyl alpha diazoacetoacetate, aliphatic azo compounds such as azobisisobutyronitrile, diazirines such as 3-trifluoromethyl-3-phenyidiazirine, ketenes (—CH=C=O) such as ketene and diphenylketene, photoactivatable ketones such as benzophenone and acetophenone, peroxy compounds such as di-t-tutyl peroxide, dicyclohexyl peroxide, diacyl peroxides such as dibenzoyl peroxide and diacetyl peroxide, and peroxyesters such as ethyl peroxybenzoate.

In the case of a vinyl group being the reactive, functional group, the reactivity of the vinyl group in a chemical species, such as e.g. divinyl sulfone, will generally require that the reactive functionality on the polymeric carrier, i.e. the group with which a vinyl group of e.g. a divinyl sulfone will react to form a covalent bond, is a nucleophilic function.

Suitable polymeric carriers will then be, for example, polymeric carriers with functional groups such as:

i) O⁻ (e.g. deprotonated phenolic hydroxy groups, such as deprotonated aromatic hydroxy groups in tyrosine residues of polypeptides or proteins), ii) S⁻ (e.g. deprotonated thiol groups on aromatic rings or aliphatic groups, such as deprotonated thiol groups in cysteine residues of polypeptides or proteins), iii) OH (e.g. aliphatic hydroxy groups on sugar rings, such as glucose or other monosaccharide rings in oligo- or polysaccharides; or alcoholic hydroxy groups in polyols, such as polyethylene glycols; or hydroxy groups in certain amino acid residues of polypeptides or proteins, such as serine or threonine residues), iv) SH (e.g. thiol groups in cysteine residues of polypeptides or proteins), primary amino groups (e.g. in lysine or ornithine residues of polypeptides or proteins, or in amino-substituted sugar rings in certain polysaccharides or derivatives thereof, such as chitosan) or secondary amino groups (e.g. in histidine residues of polypeptides or proteins).

Accordingly, the functional group in question on molecular species in the context of the invention will also normally be a nucleophilic function, such as a nucleophilic, function of one of the above-described types.

In one embodiment the present invention relates to a kit comprising a conjugate comprising a polymeric carrier molecule to which one or more molecular species are covalently attached, each via a connecting moiety in the form of a linking group.

One type of preferred linking groups are derived from divinyl sulfone. In this case the attachment of each of the linking groups to the polymeric carrier molecule is generated by a covalent linkage formed between one of the two vinyl groups of a divinyl sulfone molecule and a reactive functionality on the carrier molecule, and the attachment of a molecular species to the linking group being via a covalent linkage formed between the other vinyl group originating from the divinyl sulfone molecule and a functional group on the molecular species.

In particularly interesting conjugates of the latter type according to the invention, the polymeric carrier molecule further has covalently attached thereto one or more moieties derived from divinyl sulfone, each of which moieties is attached via a covalent linkage formed between one of the two vinyl groups of a divinyl sulfone molecule and a reactive functionality on the polymeric carrier molecule, at least one such said moiety in its attached state having the remaining vinyl group free and capable of reaction with a further molecular species having a functional group which is reactive towards the free vinyl group.

The molecular species attached to a conjugate according to the invention may be divided up into, for example, molecular species having molecular weights of about 2,000 or below, and molecular species having molecular weights of about 2,000 or above. In the former case, the polymeric carrier molecule of the conjugate may have from 1 to about 10,000 molecular species covalently attached thereto, for example from about 10 to about 1000 molecular species such as from about 20 to about 500 molecular species covalently attached thereto. In the latter case, i.e. for molecular species of molecular weight about 2,000 or above, the polymeric carrier molecule of the conjugate may have from 1 to about 1000 molecular species covalently attached thereto, for example from 1 to about 500 molecular species, such as from 1 to about 100, from 2 to about 50, or from about 10 to about 50 molecular species covalently attached thereto.

"Polymeric carrier molecule" according to the invention is any polymer capable of binding a molecular species, or capable of modification with the purpose of binding a molecular species. Polymeric carrier molecules and conjugates comprising such polymeric carrier molecules according to the invention may be chosen from a wide variety of polymers, including:

i) natural and synthetic polysaccharides, as well as derivatives thereof, for example dextrans and dextran derivatives, starches and starch derivatives, cellulose derivatives, amylose and pectin, as well as certain natural gums and derivatives thereof, such as gum arabic and salts of alginic acid:

ii) homopoly(amino acid)s having suitable reactive functionalities, such as polylysines, polyhistidines or polyornithines;

iii) natural and synthetic polypeptides and proteins, such as bovine albumin and other mammalian albumins; and iv) synthetic polymers having nucleophilic functional groups, such as polyvinyl alcohols, polyallyl alcohol, polyethylene glycols and substituted polyacrylates.

One group of preferred polymeric carrier molecules for the purposes of the invention are polysaccharides and derivatives thereof, for example, dextrans, carboxy-methyl-dextrans, hydroxyethyl- and hydroxypropyl-starches, glycogen, agarose derivatives, and hydroxyethyl- and hydroxypropyl-celluloses.

Dextrans have proved to be a group of particularly suitable polymers in connection with the present invention, and dextrans are presently representing one group of most preferred polymers.

The conjugates according to the present invention preferably have no net charge, since the presence of a net positive or negative charge may lead, inter alia, to undesirable non-specific binding of the conjugates to substances and/or materials other than those of interest. In many cases this condition will, unless charged molecular species are introduced, be fulfilled simply by ensuring that the polymeric carrier itself possesses no net charge. In a further embodiment of the invention, the polymeric carrier molecule of a reagent or conjugate of the invention is, in its free state, substantially linear and substantially uncharged at a pH in the range of about 4 to about 10. This pH interval is of practical relevance for the vast majority of immunochemical procedures, hybridization procedures and other applications of, notably, conjugates of the invention. Among various polymers which meet this criterion, are, for example, numerous polysaccharides and polysaccharide derivatives, e.g. dextrans and hydroxyethyl- and hydroxypropylcelluloses.

Depending on the use to which a reagent or conjugate of the invention is to be put, conjugates of the invention may be based on polymeric carrier molecules having molecular weights ranging from rather low to very high. In a further embodiment of the invention the polymeric carrier molecule may have a peak molecular weight in the range of from about 1,000 to about 40,000,000.

Peak molecular weights which are of considerable interest are in the range of about 1,000 to about 80,000, and in the range of about 80,000 to about 2,000,000, A peak molecular weight of particular interest, notably in the case of dextrans as polymeric carriers, is a peak molecular weight of about 500,000.

The term "peak molecular weight" (also denoted "peak average molecular weight") as employed herein denotes the molecular weight of greatest abundance, i.e. that molecular weight (among a distribution of molecular weights) which is possessed by the greatest number of molecules in a given sample or batch of the polymer. It is quite normal to characterize numerous types of polymers in this manner, owing to the difficulty (particularly for the highest molecular weights) of obtaining or preparing polymer fractions of very narrow molecular weight distribution. In the case of numerous commercially available polymers which are of interest in the context of the invention, for example dextrans, the manufacturer or distributor will be able to provide reliable peak molecular weight data (determined, for example, by gel-permeation chromatography) which can provide a basis for the selection of a polymer fraction suitable for the preparation of a particular type of reagent or conjugate.

Peak molecular weight values cited herein refer to the peak molecular weight of the free polymer in question, and take no account of, for example, the possible formation of cross-linked polymer units, e.g. as a result of cross-inking of two or more polymer molecules by reaction with e.g. divinyl sulfone during a process according to the invention for the preparation of a reagent or conjugate of the invention; such cross-linked units will, on average, have higher molecular weights than the individual free polymer molecules from which they are formed.

Conjugates according to the present invention may be tailored to meet a very wide range of requirements with regard to peak molecular weight of the polymer and the content of free, reactive vinyl groups. A further aspect of the invention relates to conjugates comprising a polymeric carrier molecule having a peas molecular weight of about 500,000 or about 2,000,000, or having a peak molecular weight in any one of the following ranges: From about 1,000 to about 20,000, from about 20,000 to about 80,000, from about 80,000 to about 500,000; from about 500,000 to about 5,000,000: and from about 1,000,000 to about 40,000,000;

The polymeric carrier molecules preferably have a content of free, reactive vinyl groups in the range of about 1 to about 5,000 µmoles of vinyl groups per gram of polymeric carrier, such as in any of the following sub-ranges (expressed in µmoles of vinyl groups per gram of polymeric carrier) From about 1 to about 50; from about 50 to about 300: from about 300 to about 1,000; and from about 1,000 to about 5,000.

In one further embodiment of the present invention there is provided a kit comprising a conjugate comprising a polymeric carrier having i) a peak molecular weight of about 500,000 or about 2,000,000, or having a peak molecular weight in any one of the following ranges: From about 1,000 to about 20,000; about 20,000 to about 80,000: about 80,000 to about 500,000; about 500,000 to about 5,000,000; or about 5,000,000 to about 40,000,000: and ii) a total content of molecular species and, where relevant, free vinyl groups in the range of about 1 to about 5,000 µmoles of a) molecular species and, where relevant, b) vinyl groups per gram of polymeric carrier, such as in any of the following sub-ranges (expressed in µmoles of molecular species plus, where relevant, µmoles of vinyl groups per gram of polymeric carrier): From about 1 to about 50; from about 50 to about 300; from about 300 to about 1,000; or from about 1,000 to about 5,000.

The samples according to the present invention are suitably conjunctival fluid, nasal secretion, pharyngeal secretion, sputum, mouth wash, bronchial wash, cervical and vaginal secretion, urine, blood, faeces, synovia, cerebrospinal fluid, ascites, vesicles, lesion exudate, and swabs from for example ulcers or conjunctiva.

According to one embodiment of the invention there is provided a method of treatment of a RS virus infectious condition in an individual The method includes the steps of i) directly detecting a RS virus cell by a method of diagnosis according to the invention, said method in one embodiment employing the kit according to the present invention, the method further comprises the step of prophylactic treatment and/or alleviation and/or curative treatment of the infection.

In addition to detection of the RS virus related biological cell it may be convenient and advantageous to determine the presence and/or the amount of one or more inflammatory indicators, for example in order to i) assess severity, or ii) predict prognosis or severity of the RS virus infection.

Inflammatory indicators including inflammatory mediators according to the invention are selected from, but not limited to, the group consisting of cytokines and autoantibodies, including cytokines belonging to inflammatoric systems such as e.g. the IL-1 system; including IL-1α and IL-1β, IL-1ra, and autoantibodies against IL-1α, sIL1-RI and sIL1-RII, the TNFα system; including, but not limited to TNFα antagonists sTNFR p55 and p75, and IL-6 and auto-antibodies against IL-6, cytokines belonging to immunoregulatory systems such as mediators related to the Th1/Th2 balance: IL-12, sIL4R, Th1 cytokines; TNFβ (LT), INFγ, Th2 cytokines: IL-4, IL-10, and additional mediators such as e.g. IL-2, RANTES, IL-8, sIL-2R, IL-18, IFNα and eosinofil cationic protein.

The below listed cytokines represent one preferred group of inflammatory indicators according to the present invention.

| Cytokine | Produced by for example | Most important effects |
|---|---|---|
| IL-1α/IL-1β | Monocytes, macrophages, NK-cells, T- and B-cells, neutrophil granolo-cytes, keratinocytes, endothelial cells, astrocytes, fibroblasts, synovial cells, smooth muscle cells, mesangial cells | Activates T-, B- and NK-cells, endothelial cells, osteoclasts and bone marrow cells. Numerous effects on inflammatory cells, mediates fever |
| IL-1ra | Monocytes, macrophages | Antagonizes effects of IL-1α/β on receptor level |
| IcIL-1ra | Neutrophil granulocytes, keratinocytes | Is being utilised on a trial basis in patients with sepsis, chronic arthritis |
| IL-2 | Th1-cells | Enhances growth of T-, B- and NK-cells |
| IL-3 | Th2-cells, keratinocytes, mastcells | Stimulates basophilic granulocytes |
| IL-4 | Th2-cells, basophilic granulocytes and mastcells, monocytes/macrophages, B-cells | Enhances growth of T- and B-cells. Suppresses macrophage functions. Induces shift of isotype in B-cells (IgE- and IgG4-production) |
| IL-5 | Th2-cells, mastcells | Stimulates eosinophil granulocytes |
| IL-6 | Monocytes, macrophages, Th2-cells, fibroblasts, endothelial cells, certain cancer cells | As IL-1 with certain exceptions. Most important activator of acut-phase protein production from hepatocytes. Growth factor for myeloma cells |
| IL-7 | Stroma cells in bone marrow, foetal liver cells, cells in intestinal epithelium | Growth- and maturation of pre-T and pre-B-cells. Coactivates T- and NK-cells |
| IL-8 | α-chemokine | α-chemokine |
| IL-9 | Th2-cells | Growth factor for mastcells (with IL-3), T-cells, megakaryocytes, pre-erythrocytes (with erythropoietin). Coactivates mast-cells, T-cells and B-cells (IgE-production) |
| IL-10 | Monocytes, macrophages, Th0-, Th2-cells, B-cells (especially EBV[i] in-fected), mastcells, keratinocytes, epi-dermal cells | Coactivates certain T- and B-cell sub-populations and mastcells. Suppresses Th1-cells (IFNγ-production) and certain monocyte/macrophage- and NK-cell functions |
| IL-11 | Fibroblasts, stroma cells in bone mar-row, foetal lung cells, trophoblasts | As IL-6 |
| IL-12 | Monocytes, macrophages, B-cells, dendritic cells, Langerhan cells, ke-ratinocytes, neutrophil granulocytes | Activates Th1-cells (IFNγ-production) and NK-cells |
| IL-13 | T-cells | Stimulates B-cell growth (induces IgE, IgG4) |
| IL-14 | T-cells | Coactivates B-cells (prolifera-tion/differentiation), but inhibits Ig-secretion |
| IL-15 | Monocytes, macrophages, certain T-cells, fibroblasts, endothelial and epithelial cells, myocytes, stroma cells in bone marrow, placenta cells | As IL-2 |
| IL-16 | T-cells, eosinophil granulocytes | Chemotactic for CD4 T-cells. Activates CD4 T-cells and monocytes |
| IL-17 | Th-cells | Activates T-cells, fibroblasts (ICAM-1 ex-pression). Induces IL-6 and IL-8 |
| IL-18 | Monocytes, macrophages, Kupffer cells, osteoblasts | Activates Th1- and NK-cells (induces IFNγ) |
| LIF | Monocytes, macrophages, T-cells, stroma cells in bone marrow, fibro-blasts, astrocytes | As IL-6 |
| PDGF | Thrombocytes, monocytes, macro-phages, endothelial cells, smooth muscle cells, fibroblasts, neurons | Activates vascular smooth muscle cells, endothelial- and epithelial cells, gliacells, chondrocytes, fibroblasts, neutrophilocytes and monocytes. Chemotactic for the above mentioned cells |
| NGF | Macrophages, astrocytes, nerve cells, smooth muscle cells, fibroblasts | Activates B-cells, basophilic granulocytes and sympathetic and sensory neurons |
| TGFβ (sev-eral forms) | Megakaryocytes, thrombocytes, monocytes, macrophages, T-cells, endothelial cells, fibroblasts, osteo-blasts, chondrocytes, smooth muscle cells | Activates B-cells (induces (IgA), osteo-blasts, fibroblasts and other cells. Inhibits growth of endothelial and epithelial cells, osteoclasts, T-cells and NK-cells |
| TNF | Monocytes, macrophages incl. tissue macrophages, Th1- and Tc-cells, B-cells, NK-cells, neutrophilocytes, ke- | Activates T-, B- and NK-cells, neutro- and eosinophil granulocytes, endothelial cells, osteoclasts. |

-continued

| Cytokine | Produced by for example | Most important effects |
|---|---|---|
| | ratinocytes, smooth muscle cells | Cytotoxic for transformed and virus infected cells. Mediates fever |
| LTα/LTβ | Th1-cells, (B-cells) | As TNF |
| FasL | Th1- and Tc-cells, NK-cells | Cytotoxic for virus infected cells, incl. HIV-infected cells |
| IFNα (>16 subtypes) | Virus infected leukocytes, T- and B-cells, monocytes, macrophages | Antiviral activity. Antiproliferative and antitumour effects. Activates macrophages, NK-cells and B-cells |
| IFNβ | Many virus infected cell types, fibroblasts | Antiviral activity. Activates NK-cells |
| IFNγ | Th-1- and Tc-cells, endothelial cells, smooth muscle cells | Activates fibroblasts, monocytes/ macrophages, T-, B- and NK-cells (induces IgG). Induces MHC II (many cell types). Suppresses cell growth in general |
| SCF | Stroma cells in bone marrow, endothelial cells, fibroblasts, Sertoli cells | Activates and differentiates marrow stem-cells, mastcells |
| GM-CSF | Th2- cells, fibroblasts, endothelial cells, macrophages, mastcells, neutrophil granulocytes, eosinophil granulocytes | Activates, differentiates precursors of T-cells, monocytes, neutrophil granulocytes |
| G-CSF | Monocytes, macrophages, fibroblasts, endothelial cells, T-cells, neutrophil granulocytes | Activates, differentiates precursors of neutrophil granulocytes |
| M-CSF | Monocytes, macrophages, fibroblasts, endothelial cells | Activates, differentiates precursors of monocytes |
| α-chemokines (CXC) | Monocytes, macrophages, T-cells, endothelial cells, several other cells | Chemotactic for neutrophil granulocytes, T-cells, basophilic granulocytes, keratinocytes |
| β-chemokines (CC) | Monocytes, macrophages, T- and B-cells, thrombocytes, endothelial cells, smooth muscle cells, mastcells, fibroblasts | Chemotactic for monocytes/macrophages, NK-cells, eosinophil and basophilic granulocytes. Inhibits infection of CD4-positive monocytes/macrophages with HIV (that uses β-chemokine receptors as co-activators by the infection) |
| Lymfotactin | T-cells | Chemotactic for T-cells |
| VIP/PACAP and other neuropeptides | Nerve cells (in for example thymus, spleen and lymphnodes), T- and B-cells, eosinophilocytes, mastcells, neutrophilocytes | Immunosuppressive by inhibition of IL-2 and IL-4 production. Indirect immunostimulation by inhibition of IL-10 |

| Abbreviations and definitions | |
|---|---|
| CC: | β-chemokines (for example macrophage inflammatory protein (MIP)-1, monocyte chemoattractant protein (MCP)-1-4, regulated on activation, normal T expressed and secreted (RANTES) |
| CXC: | α-chemokines (for example IL-8) |
| CSF: | colony-stimulating factor |
| FasL: | Fas-ligand |
| G-CSF: | granolocyte-CSF |
| GM-CSF: | granolocyte-macrophage-CSF |
| icIL-1ra: | intracellular IL-1ra |
| IFN: | interferon |
| IL: | interleukine |
| LT: | lymphotoxin |
| M-CSF: | macrophage-CSF |
| MHC: | major histocompatibility complex |
| NGF: | nerve growth factor |
| NK-cells: | natural killer cells |
| PACAP: | pituitary adenylyl cyclase-activating peptide |
| SCF: | stem-cell factor |
| TGF: | transforming growth factor |
| TNF: | tumour necrosis factor |
| VIP: | vasoactive intestinal peptide |

In particular the present invention may be used for providing a cytokine profile, i.e. a measurement of at least two cytokines, such as for example at least four cytokines, whereby the presence and relative concentration of each cytokine may be indicative of a disease or of the prognosis of a disease.

EXAMPLE 1

Dipstick for Detecting RS Virus in a Sample

A dipstick for detecting RS virus in a sample that could clearly detect RS virus, by the appearance of a clear visually detectable signal, such as a red spot in a functional lateral flow assay was developed.

The antigen to be tested is a commercially available antigen (Chemicon, RSV, long AG 857).

A monoclonal antibody directed to F-glycoprotein as the targeting species coupled to the solid surface on the dipstick, the so-called catching antibody was used.

The reporter species further comprised polydextran polymeric carrier molecules, which were of approximately 500, 000 Da, to which the reactive group divinylsulphone were covalently attached. Furthermore, the reporter species comprised rhodamine label molecules, which were also attached via the divinylsulphone groups.

To test the reporter species a 2-layer lateral flow test was employed, following the principles outlined in FIG. 1. FIG. 1 illustrates a schematic dipstick, for use in an assay for testing detecting of RS related cell in a sample. The dipstick comprises an application zone for the sample comprising the reporter species. The term conjugate refers to reporter species. Furthermore, the dipstick comprises one zone whereto the catching antibody is coupled and a second zone whereto the control antibody is coupled. The dipstick is made of nitrocellulose (Sartonius Unisart CN200), and of a microporous membrane of Whatman FO 75-17 or Millipore Rapid Q24, and an absorbent pad (Whatman 1,5 NF).

A secondary antibody with specificity against the targeting antibody comprised within the reporter species was used as catching antibody. This lateral test gave a positive red spot, which showed that 1) targeting antibody was coupled to polydextran carrier, 2) the polydextran carrier had good flow characteristics. Furthermore, none of them gave rise to background/unspecific binding.

The test was developed so that a visually visible red spot appears when the test is positive. This spot is produced by accumulation of rhodamine linked to the reporter species. The positive result in the test is defined as samples comprising RS virus. A negative result, which is visualised by no colour change (no red spot appear), was obtained when substantially no RS virus was used.

The test is a 1-step test, where sample is applied directly to the dipstick after which the test results appear. When the test is performed as a 1-step test the first colour reaction appear on the flow test as early as after 1–3 minutes. The test is finished after about 5 minutes.

A control antibody that binds the reporter species independently of the antigen in the urine, was also coupled to the solid surface of the dipstick within the control zone. A red control spot appeared every time in the test regardless whether negative urine or positive urine was used, as an indicator of whether the test was correctly performed. The red colour of this control spot was also produced by accumulation of rhodamine linked to the reporter species.

Furthermore, a dipstick has been developed so that a red test line appears across the membrane instead of a red spot, both for observing the test result and the control (FIG. 2). Often it is observed that the colour intensity is increased on a test line compared to a test spot.

EXAMPLE 2

Competitive Dipstick

In this example a dipstick similar to the dipstick described in Example 1 was produced as a competitive dipstick whereby a positive signal is shown as no change of colour, whereas a negative signal is shown as a colour change.

The amount of reporter species was titrated in a way such as a red spot (visible accumulation of rhodamine) only appeared in negative samples.

What is claimed is:

1. A kit for directly detecting a respiratory syncytial (RS) virus infected cell or an RS virus biological particle present in a sample in an amount of less than about 2000 cells or particles per microlitre ($10^{-6}$ liter), said kit comprising i) a solid support comprising an application zone for applying the sample and a separate detection zone, and ii) a conjugate comprising a polymeric carrier molecule bound to a) at least one targeting species capable of directly binding an RS virus infected cell or RS virus biological particle, and b) at least one labelling species, wherein the application zone and the detection zone can form a liquid contact, the application zone comprises at least one of said conjugate, said conjugate being movable, and the detection zone comprises at least one targeting species which is bound to the solid support and is capable directly of binding an RS virus infected cell or RS virus biological particle.

2. Kit according to claim 1, wherein the conjugate further comprises ii) at least one connecting moiety foreign to the polymeric carrier molecule, and covalently attaching it to a targeting species or a labelling species.

3. Kit according to claim 2, wherein the polymeric carrier molecule comprises connecting moieties in an amount of from about 5 to about 5,000 μmoles per gram of polymeric carrier.

4. Kit according to claim 1, wherein the targeting species is selected from monoclonal and polyclonal antibodies.

5. Kit according to claim 4, wherein the targeting species is an antibody recognising a nucleoprotein of RS virus or a glycoprotein of RS virus.

6. Kit according to claim 1, wherein the labelling species is selected from the group consisting of proteins; enzymes; toxins; drugs; dyes; fluorescent, luminescent, phosphorescent and other light-emitting substances; cells; metal-chelating substances; substances labelled with a radioactive isotope; and substances labelled with a heavy atom.

7. Kit according to claim 1, wherein the labelling species is selected from the group consisting of ferritin, phycoerythrins, phycocyanins, phycobilins, horseradish peroxidase, alkaline phosphatase, glucose oxidases, galactosidases, ureases, iminodiacetic acid, ethylenediaminetetraacetic acid, diethylenetriaminepentaacetic acid, and desferrioxamine B.

8. The kit according to claim 1 where at least one molecule of said conjugate comprises a plurality of targeting species.

9. Kit according to claim 8, wherein the targeting species attached to said molecule of conjugate are identical.

10. Kit according to claim 8, wherein the targeting species attached to said molecule of conjugate are non-identical.

11. Kit according to claim 2, wherein the polymeric carrier is selected from the group consisting of natural and synthetic polysaccharides; homopoly amino acids; natural and synthetic polypeptides and proteins; and synthetic polymers having nucleophilic functional groups.

12. Kit according to claim 2, wherein the polymeric carrier is selected from the group consisting of polyvinyl alcohols, polyallyl alcohols, polyethylene glycols and substituted polyacrylates.

13. Kit according to claim 2, wherein the polymeric carrier is selected from the group consisting of dextrans, carboxymethyl-dextrans, starches, hydroxyethyl-starches, hydroxypropyl-starches, glycogen, agarose derivatives, cellulose derivatives and natural gums.

14. Kit according to claim 13, wherein the polymeric carrier is a dextran.

15. Kit according to claim 13, wherein the polymeric carrier is selected from the group consisting of hydroxyethyl-celluloses and hydroxypropyl-celluloses.

16. Kit according to claim 1, said kit being a dip-stick.

17. Kit according to claim 1, said kit being adapted for a microsystem.

18. Kit according to claim 1, further comprising means for detecting at least one inflammatory indicator.

19. Kit according to claim 18, wherein the at least one inflammatory indicator is a cytokine.

20. Kit according to claim 19, comprising means for detecting at least 3 different cytokines.

21. The kit according to claim 1 further comprising a positive control zone comprising means for generating a positive control confirming the transfer of at least part of said sample from said application zone to said detection zone.

22. The kit of claim 1 in which at least one molecule of conjugate comprises a plurality of labeling species.

23. The kit of claim 22 in which the labeling species attached to said molecule are identical.

24. The kit of claim 1 in which the labeling species is a fluorescent substance.

25. The kit of claim 24 in which the labeling species is rhodamine.

26. The kit of claim 1 in which the polymeric carrier is a polysaccharide.

27. The kit of claim 26 in which the polymeric carrier is a polydextran.

28. The kit of claim 24 in which the polymeric carrier is a polysaccharide.

29. The kit of claim 28 in which the polymeric carrier is a polydextran.

30. The kit of claim 1 in which the targeting species is an antibody.

31. The kit of claim 29 in which the targeting species is an antibody.

32. The kit of claim 1 wherein said detection zone is free of said conjugate until said sample is applied, said sample causing the fluid movement of said conjugate from the application zone to the detection zone.

33. The kit of claim 1 wherein said conjugate has a predetermined peak molecular weight of from about 1,000 to about 40,000,000.

34. The kit of claim 1 wherein said conjugate has a predetermined peak molecular weight of from about 1,000 to about 20,000.

35. The kit of claim 1 wherein said conjugate has a predetermined peak molecular weight of from about 20,000 to about 80,000.

36. The kit of claim 1 wherein said conjugate has a predetermined peak molecular weight of from about 80,000 to about 500,000.

37. The kit of claim 1 wherein said conjugate has a predetermined peak molecular weight of from about 500,000 to about 5,000,000.

38. The kit of claim 33 wherein said conjugate has a predetermined peak molecular weight of from about 5,000,000 to about 40,000,000.

39. The kit of claim 1 wherein said conjugate comprises non-cross-linked units of polymers and cross-linked polymer units.

40. The kit of claim 1 wherein said conjugate is applied to the solid support followed by drying the solid support.

41. Method of detecting a predetermined RS virus infected cell or RS virus biological particle present in a sample, said method comprising the steps of
   i) providing a kit according to claim 1
   ii) contacting the sample with the kit of step i), and
   iii) detecting, in said detection zone, the presence of a conjugate binding the predetermined RS virus infected cell or RS virus biological particle,
   wherein the detection of the conjugate is indicative of the presence of the RS virus infected cell or RS virus biological particle in the sample.

42. Method according to claim 41, wherein the sample is a body fluid sample.

43. Method according to claim 41, said kit further comprising means for detecting at least one predetermined inflammatory indicator.

44. Method according to claim 43, wherein the inflammatory indicator is present in the sample in an amount of less than about 100 nanograms ($100 \times 10^{-9}$ grams) per milliliter ($10^{-3}$ liter).

45. Method according to claim 41, wherein the polymeric carrier molecule comprises i) a plurality of at least one connecting moiety attached to polymeric carrier group, and ii) at least one molecular species selected from the group consisting of targeting species and labelling species, wherein each of the molecular species is attached to at least one connecting moiety attached to the polymeric carrier molecule.

46. Method according to claim 41, wherein the labelling species is selected from the group consisting of proteins; enzymes; toxins; drugs; dyes; fluorescent, luminescent, phosphorescent and other light-emitting substances; metal-chelating substances; substances labelled with a radioactive isotope; and substances labelled with a heavy atom.

47. Method according to claim 41, wherein the labelling species is selected from the group consisting of ferritin, phycoerythrins, phycocyanins, phycobilins, horseradish peroxidase, alkaline phosphatase, glucose oxidases, galactosidases, ureases, iminodiacetic acid, ethylenediaminetetraacetic acid, diethylenetriaminepentaacetic acid, and desferrioxamine B.

48. Method according to claim 41, wherein the polymeric carrier is selected from the group consisting of natural and synthetic polysaccharides; homopoly amino acids; natural and synthetic polypeptides and proteins; and synthetic polymers having nucleophilic functional groups.

49. Method according to claim 41, wherein the polymeric carrier is selected from the group consisting of polyvinyl alcohols, polyallyl alcohols, polyethylene glycols and substituted polyacrylates.

50. Method according to claim 41, wherein the polymeric carrier is selected from the group consisting of dextrans, carboxymethyl-dextrans, starches, hydroxyethyl-starches, hydroxypropyl-starches, glycogen, agarose derivatives, cellulose derivatives and natural gums.

51. Method according to claim 50, wherein the polymeric carrier is a dextran.

52. Method according to claim 41, wherein the polymeric carrier is selected from the group consisting of hydroxyethyl-celluloses and hydroxypropyl-celluloses.

53. Method according to claim 43, wherein the predetermined inflammatory indicator is selected from the group consisting of agonists from the IL-1 system, autoantibodies against IL-1α, sIL1-RI and sIL1-RII.

54. Method according to claim 43, wherein the predetermined inflammatory indicator is selected from the group consisting of agonists from the TNFα system.

55. Method according to claim 43, wherein the predetermined inflammatory indicator is selected from the group consisting of IL-6 and autoantibodies against IL-6.

56. Method according to claim 43, wherein the predetermined inflammatory indicator is selected from the group consisting of IL-12, sIL-4R, TNFβ (LT), INFγ, IL-4, and IL-10.

57. Method according to claim 43, wherein the predetermined inflammatory indicator is selected from the group consisting of IL-2, RANTES, IL-8, sIL-2R, IL-18, IFNα, and eosinophil cationic protein.

58. The method of claim 41, said kit further comprising a positive control zone comprising means for generating a positive control confirming the transfer of at least part of said sample from said application zone to said detection zone.

59. The method of claim 41 wherein said detection zone is free of said conjugate until said sample is applied, said sample causing the fluid movement of said conjugate from the application zone to the detection zone.

60. The method of claim 41 wherein said conjugate has a predetermined peak molecular weight of from about 1,000 to about 40,000,000.

61. The method of claim 41 wherein said conjugate has a predetermined peak molecular weight of from about 1,000 to about 20,000.

62. The method of claim 41 wherein said conjugate has a predetermined peak molecular weight of from about 20,000 to about 80,000.

63. The method of claim 41 wherein said conjugate has a predetermined peak molecular weight of from about 80,000 to about 500,000.

64. The method of claim 41 wherein said conjugate has a predetermined peak molecular weight of from about 500,000 to about 5,000,000.

65. The method of claim 41 wherein said conjugate has a predetermined peak molecular weight of from about 5,000,000 to about 40,000,000.

66. The method of claim 41 wherein said conjugate comprises non-cross-linked units of polymers and cross-linked polymer units.

67. The method of claim 41 wherein said conjugate is applied to the solid support followed by drying the solid support.

68. A method for diagnosing a RS virus infectious condition in an individual, said method comprising the steps of (a) providing a kit according to claim 1 for directly detecting a RS virus infected cell or RS virus biological particle present in a sample in an amount of less than about 2000 cells or particles per microlitre ($10^{-6}$ litre), (b) contacting the sample with the kit of step (a)

(c) detecting, in the detection zone, the presence of a conjugate capable of binding the predetermined RS virus infected cell or RS virus biological particle, wherein the detection of the conjugate is indicative of the presence of the RS virus infected cell or RS virus biological particle in the sample and wherein detecting the presence of the RS virus infected cell or RS virus biological particle is indicative of an infectious condition, and (d) diagnosing said infectious condition.

69. The method according to claim 68 further comprising the step of detecting a predetermined inflammatory indicator present in a body fluid sample prior to diagnosing said infectious condition.

70. The method of claim 69, said kit further comprising a positive control zone comprising means for generating a positive control confirming the transfer of at least part of said sample from said application zone to said detection zone.

* * * * *

UNITED STATES PATENT AND TRADEMARK OFFICE
CERTIFICATE OF CORRECTION

PATENT NO.    : 6,790,611 B2
DATED         : September 14, 2004
INVENTOR(S)   : Michael Rud Lassen and Morten Breindahl It is certified that error appears in the above-identified patent and that said Letters Patent is hereby corrected as shown below:

Column 41,
Line 59, delete "33" and insert therefor -- 1 --

Signed and Sealed this

Twenty-sixth Day of April, 2005

JON W. DUDAS
*Director of the United States Patent and Trademark Office*